US011071637B2

(12) United States Patent
Dawson et al.

(10) Patent No.: US 11,071,637 B2
(45) Date of Patent: Jul. 27, 2021

(54) MEDICAL DEVICE DELIVERY

(71) Applicant: Covidien LP, Mansfield, MA (US)

(72) Inventors: Marc Dawson, Mission Viejo, CA (US); Ashok Nageswaran, Irvine, CA (US); Aaron Barrett, San Clemente, CA (US); Hieu Dang, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 98 days.

(21) Appl. No.: 15/951,779

(22) Filed: Apr. 12, 2018

(65) Prior Publication Data

US 2019/0314175 A1 Oct. 17, 2019

(51) Int. Cl.

*A61F 2/95* (2013.01)
*A61F 2/90* (2013.01)
*A61F 2/06* (2013.01)

(52) U.S. Cl.

CPC .................. *A61F 2/95* (2013.01); *A61F 2/90* (2013.01); *A61F 2/06* (2013.01); *A61F 2/9517* (2020.05); *A61F 2002/9511* (2013.01)

(58) Field of Classification Search

CPC ................ A61F 2/95; A61F 2002/9665; A61F 2002/9505; A61F 2002/9511
USPC .......................................................... 623/1.11
See application file for complete search history.

(56) References Cited

U.S. PATENT DOCUMENTS 3,416,531 A 12/1968 Edwards
4,364,391 A 12/1982 Toye
4,425,919 A 1/1984 Alston, Jr. et al.
4,516,972 A 5/1985 Samson
4,655,771 A 4/1987 Wallsten
(Continued)

FOREIGN PATENT DOCUMENTS

CN 104582643 A 4/2015
CN 105232195 A 1/2016
(Continued)

OTHER PUBLICATIONS

International Search Report and Written Opinion dated Oct. 15, 2020, International Application No. PCT/US20/70151, 110 pages.
(Continued)

*Primary Examiner* — Elizabeth Houston
*Assistant Examiner* — Alyssa M Keane
(74) *Attorney, Agent, or Firm* — Fortem IP LLP; Matthew Lincicum; Katrina Henrikson

(57) ABSTRACT

A stent delivery system includes a core member and a coupling assembly rotatably coupled to the core member distal segment. The coupling assembly includes first and second plates and first and second spacers. The first plate is rotatably coupled to the core member and includes an outer surface having three or more projections separated by recesses. The first spacer is coupled to the core member and disposed between the first plate and a proximal restraint. The second plate is rotatably coupled to the core member and includes an outer surface having three or more projections separated by recesses. The second spacer is coupled to the core member and disposed between the first plate and the second plate. A stent extends along the core member distal segment such that an inner surface of the stent is engaged by one or more projections of the first plate or the second plate.

24 Claims, 9 Drawing Sheets

(56) References Cited

U.S. PATENT DOCUMENTS 4,723,936 A 2/1988 Buchbinder et al.
4,877,031 A 10/1989 Conway et al.
4,990,151 A 2/1991 Wallsten
5,011,478 A 4/1991 Cope
5,026,377 A 6/1991 Burton et al.
5,037,404 A 8/1991 Gold et al.
5,061,275 A 10/1991 Wallsten et al.
5,098,393 A 3/1992 Amplatz et al.
5,108,411 A 4/1992 Mkenzie et al.
5,147,370 A 9/1992 McNamara et al.
5,178,158 A 1/1993 de Toledo
5,201,316 A 4/1993 Pomeranz et al.
5,209,734 A 5/1993 Hurley et al.
5,279,562 A 1/1994 Sirhan et al.
5,279,596 A 1/1994 Castaneda et al.
5,292,311 A 3/1994 Cope
5,318,032 A 6/1994 Lonsbury et al.
5,318,525 A 6/1994 West
5,318,529 A 6/1994 Kontos
5,358,493 A 10/1994 Schweich, Jr. et al.
5,382,259 A 1/1995 Phelps et al.
5,403,292 A 4/1995 Ju
5,437,288 A 8/1995 Schwartz et al.
5,445,646 A 8/1995 Euteneuer et al.
5,454,795 A 10/1995 Samson
5,458,605 A 10/1995 Klemm
5,474,563 A 12/1995 Mvler et al.
5,478,349 A 12/1995 Nicholas
5,484,444 A 1/1996 Braunschweiler et al.
5,496,294 A 3/1996 Hergenrother et al.
5,499,975 A 3/1996 Cope et al.
5,522,822 A 6/1996 Phelps et al.
5,531,721 A 7/1996 Peoin et al.
5,534,007 A 7/1996 St. Germain et al.
5,545,209 A 8/1996 Roberts et al.
5,554,139 A 9/1996 Okajima
5,569,220 A 10/1996 Webster, Jr.
5,571,135 A 11/1996 Fraser et al.
5,573,520 A 11/1996 Schwartz et al.
5,584,821 A 12/1996 Hobbs et al.
5,599,325 A 2/1997 Ju et al.
5,599,326 A 2/1997 Carter
5,601,539 A 2/1997 Corso, Jr.
5,636,641 A 6/1997 Fariabi
5,645,559 A 7/1997 Hachtman et al.
5,658,264 A 8/1997 Samson
5,662,622 A 9/1997 Gore et al.
5,676,659 A 10/1997 McGurk
5,695,483 A 12/1997 Samson
5,695,499 A 12/1997 Helqerson et al.
5,702,373 A 12/1997 Samson
5,702,418 A 12/1997 Ravenscroft
5,704,926 A 1/1998 Sutton
5,709,703 A 1/1998 Lukic et al.
5,711,909 A 1/1998 Gore et al.
5,725,513 A 3/1998 Ju et al.
5,725,571 A 3/1998 Imbert et al.
5,728,063 A 3/1998 Preissman et al.
5,741,429 A 4/1998 Donadio, III et al.
5,743,876 A 4/1998 Swanson
5,755,777 A 5/1998 Chuter
5,759,173 A 6/1998 Preissman et al.
5,776,141 A 7/1998 Klein et al.
5,782,811 A 7/1998 Samson et al.
5,791,036 A 8/1998 Goodin et al.
5,824,041 A 10/1998 Lenker et al.
5,833,632 A 11/1998 Jacobsen et al.
5,836,925 A 11/1998 Soltesz
5,836,926 A 11/1998 Peterson et al.
5,851,203 A 12/1998 van Muiden
5,853,400 A 12/1998 Samson
5,873,866 A 2/1999 Kondo et al.
5,876,386 A 3/1999 Samson
5,891,112 A 4/1999 Samson
5,897,529 A 4/1999 Ponzi
5,897,537 A 4/1999 Berg et al.
5,902,290 A 5/1999 Peacock, III et al.
5,906,605 A 5/1999 Coxum
5,935,161 A 8/1999 Robinson et al.
5,938,653 A 8/1999 Pepin
5,951,494 A 9/1999 Wana et al.
5,951,539 A 9/1999 Nita et al.
5,961,510 A 10/1999 Fugoso et al.
5,968,053 A 10/1999 Revelas
5,968,069 A * 10/1999 Dusbabek .............. A61F 2/958 606/194
5,971,975 A 10/1999 Mills et al.
6,017,323 A 1/2000 Chee
6,030,371 A 2/2000 Pursley
6,045,547 A 4/2000 Ren et al.
6,053,903 A 4/2000 Samson
6,053,904 A 4/2000 Scribner et al.
6,077,258 A 6/2000 Lange et al.
6,077,295 A 6/2000 Limon et al.
6,077,297 A 6/2000 Robinson et al.
6,083,152 A 7/2000 Strong
6,093,177 A 7/2000 Javier, Jr. et al.
6,105,651 A 8/2000 Leanna
6,106,510 A 8/2000 Lunn et al.
6,106,540 A 8/2000 White et al.
6,123,723 A 9/2000 Konya et al.
6,126,685 A 10/2000 Lenker et al.
6,135,992 A 10/2000 Wang
6,149,680 A 11/2000 Shelso et al.
6,152,912 A 11/2000 Jansen et al.
6,152,944 A 11/2000 Holman et al.
6,159,219 A 12/2000 Ren
6,165,163 A 12/2000 Chien et al.
6,165,166 A 12/2000 Samuelson et al.
6,171,295 B1 1/2001 Garabedian et al.
6,171,296 B1 1/2001 Chow
6,171,297 B1 1/2001 Pedersen et al.
6,186,986 B1 2/2001 Berg et al.
6,193,739 B1 2/2001 Chevillon et al.
6,197,015 B1 3/2001 Wilson
6,217,565 B1 4/2001 Cohen
6,217,566 B1 4/2001 Ju et al.
6,251,132 B1 6/2001 Ravenscroft et al.
6,258,080 B1 7/2001 Samson
6,264,683 B1 7/2001 Stack et al.
6,287,315 B1 9/2001 Wiieratne et al.
6,325,807 B1 12/2001 Que
6,350,278 B1 2/2002 Lenker et al.
6,355,027 B1 3/2002 Le et al.
6,358,238 B1 3/2002 Sherry
6,358,460 B1 3/2002 Hunt, Jr. et al.
6,368,316 B1 4/2002 Jansen et al.
6,371,953 B1 4/2002 Beyar et al.
6,383,171 B1 5/2002 Gifford et al.
6,387,118 B1 5/2002 Hanson
6,389,087 B1 5/2002 Heinonen et al.
6,395,008 B1 5/2002 Ellis et al.
6,395,017 B1 5/2002 Dwyer et al.
6,398,791 B1 6/2002 Que et al.
6,419,693 B1 7/2002 Fariabi
6,425,898 B1 7/2002 Wilson et al.
6,428,552 B1 8/2002 Sparks
6,443,971 B1 9/2002 Boylan et al.
6,458,075 B1 10/2002 Sugiyama et al.
6,464,684 B1 10/2002 Galdonik
6,468,298 B1 10/2002 Pelton
6,475,184 B1 11/2002 Wang et al.
6,494,907 B1 12/2002 Bulver et al.
6,508,804 B2 1/2003 Sarge et al.
6,508,805 B1 1/2003 Garabedian et al.
6,508,806 B1 1/2003 Hoste
6,517,547 B1 2/2003 Feeser et al.
6,554,820 B1 4/2003 Wendlandt et al.
6,562,021 B1 5/2003 Derbin et al.
6,562,063 B1 5/2003 Euteneuer et al.
6,576,006 B2 6/2003 Limon et al.
6,582,460 B1 6/2003 Cryer
6,589,227 B2 7/2003 Soslashednderskov Klint
6,602,271 B2 8/2003 Adams et al.

(56) References Cited

U.S. PATENT DOCUMENTS 6,607,551 B1 8/2003 Sullivan et al.
6,622,367 B1 9/2003 Bolduc et al.
6,635,047 B2 10/2003 Forsberg
6,638,245 B2 10/2003 Miller et al.
6,641,564 B1 11/2003 Kraus
6,648,654 B1 11/2003 Akram et al.
6,648,874 B2 11/2003 Parisi et al.
6,652,508 B2 11/2003 Griffin et al.
6,663,614 B1 12/2003 Carter
6,669,719 B2 12/2003 Wallace et al.
6,689,120 B1 2/2004 Gerdts
6,699,274 B2 3/2004 Stinson
6,702,782 B2 3/2004 Miller et al.
6,706,055 B2 3/2004 Douk et al.
6,716,207 B2 4/2004 Farnholtz
6,726,659 B1 4/2004 Stocking et al.
6,764,504 B2 7/2004 Wanq et al.
6,808,529 B2 10/2004 Fulkerson
6,814,749 B2 11/2004 Cox et al.
6,815,325 B2 11/2004 Ishii
6,817,995 B1 11/2004 Halpern
6,830,575 B2 12/2004 Stenzel et al.
6,837,890 B1 1/2005 Chludzinski et al.
6,843,802 B1 1/2005 Villalobos et al.
6,858,024 B1 2/2005 Berg et al.
6,866,660 B2 3/2005 Garabedian et al.
6,866,679 B2 3/2005 Kusleika
6,932,837 B2 8/2005 Amplatz et al.
6,939,353 B2 9/2005 Que et al.
6,945,970 B2 9/2005 Pepin
6,960,227 B2 11/2005 Jones et al.
6,984,963 B2 1/2006 Pidutti et al.
6,989,024 B2 1/2006 Hebert et al.
7,001,369 B2 2/2006 Griffin et al.
7,011,675 B2 3/2006 Hemerick et al.
7,025,758 B2 4/2006 Klint
7,074,236 B2 7/2006 Rabkin et al.
7,104,979 B2 9/2006 Jansen et al.
7,147,656 B2 12/2006 Andreas et al.
7,156,860 B2 1/2007 Wallsten
7,163,523 B2 1/2007 Devens, Jr. et al.
7,166,088 B2 1/2007 Heuser
7,166,099 B2 1/2007 Devens, Jr.
7,166,100 B2 1/2007 Jordan et al.
7,172,575 B2 2/2007 El-Nounou et al.
7,223,263 B1 5/2007 Seno
7,228,878 B2 6/2007 Chen et al.
7,306,624 B2 12/2007 Yodfat et al.
7,323,000 B2 1/2008 Monstdt et al.
7,331,948 B2 2/2008 Skarda
7,357,812 B2 4/2008 Andreas et al.
7,371,248 B2 5/2008 Dapolito et al.
7,402,151 B2 7/2008 Rosenman et al.
7,404,820 B2 7/2008 Mazzocchi et al.
7,427,288 B2 9/2008 Sater
7,438,712 B2 10/2008 Chouinard
7,445,684 B2 11/2008 Pursley
7,473,271 B2 1/2009 Gunderson
7,473,272 B2 1/2009 Pryor
7,481,804 B2 1/2009 Devens, Jr.
7,507,229 B2 3/2009 Hewitt et al.
7,524,322 B2 4/2009 Monstdt et al.
7,556,634 B2 7/2009 Lee et al.
7,556,710 B2 7/2009 Leeflang et al.
7,569,046 B2 8/2009 Zhou
7,572,290 B2 8/2009 Yodfat et al.
7,582,079 B2 9/2009 Wendlandt et al.
7,597,830 B2 10/2009 Zhou
7,621,904 B2 11/2009 Mcferran et al.
7,641,646 B2 1/2010 Kennedy, II
7,651,520 B2 1/2010 Fischell et al.
7,655,031 B2 2/2010 Tenne et al.
7,674,411 B2 3/2010 Berg et al.
7,691,138 B2 4/2010 Stenzel et al.
7,708,704 B2 5/2010 Mitelberg et al.
7,717,953 B2 5/2010 Kaolan et al.
7,740,652 B2 * 6/2010 Gerdts ..................... A61F 2/95 623/1.11
7,758,624 B2 7/2010 Dorn et al.
7,766,820 B2 8/2010 Core
7,766,896 B2 8/2010 Kornkven Volk et al.
7,780,646 B2 8/2010 Farnholtz
7,815,600 B2 10/2010 Al-Marashi et al.
7,815,608 B2 10/2010 Schafersman et al.
7,815,628 B2 10/2010 Devens, Jr.
7,828,790 B2 11/2010 Griffin
7,867,267 B2 1/2011 Sullivan et al.
7,879,022 B2 2/2011 Bonnette et al.
7,935,140 B2 * 5/2011 Griffin ..................... A61F 2/95 623/1.11
7,942,925 B2 5/2011 Yodfat et al.
7,955,370 B2 6/2011 Gunderson
7,981,148 B2 7/2011 Aquilar et al.
7,993,385 B2 8/2011 Levine et al.
8,025,692 B2 9/2011 Feeser
8,034,095 B2 10/2011 Randolph et al.
8,042,720 B2 10/2011 Shifrin et al.
8,048,104 B2 11/2011 Monstadt et al.
8,066,754 B2 11/2011 Malewicz
8,083,791 B2 12/2011 Kaplan et al.
8,088,140 B2 1/2012 Ferrera et al.
8,092,508 B2 1/2012 Leynov et al.
8,109,987 B2 2/2012 Kaplan et al.
8,133,266 B2 3/2012 Thomas et al.
8,147,534 B2 4/2012 Berez et al.
8,187,314 B2 5/2012 Davis et al.
8,257,432 B2 9/2012 Kaplan et al.
8,298,276 B2 10/2012 Ozawa et al.
8,317,850 B2 11/2012 Kusleika
8,337,543 B2 * 12/2012 Jordan ..................... A61F 2/95 623/1.12
8,366,763 B2 2/2013 Davis et al.
8,382,818 B2 2/2013 Davis et al.
8,480,701 B2 7/2013 Monstadt
8,579,958 B2 11/2013 Kusleika
8,591,566 B2 11/2013 Newell et al.
8,597,321 B2 12/2013 Monstadt et al.
8,636,760 B2 1/2014 Garcia et al.
8,679,172 B2 3/2014 Dorn et al.
8,790,387 B2 7/2014 Nguyen et al.
8,858,613 B2 10/2014 Cragg et al.
8,968,383 B1 3/2015 Johnson et al.
9,072,624 B2 7/2015 Brown et al.
9,393,141 B2 7/2016 Gerdts et al.
9,439,795 B2 9/2016 Wang et al.
10,786,377 B2 9/2020 Nageswaran et al.
2001/0020173 A1 9/2001 Klumb et al.
2001/0027310 A1 10/2001 Parisi et al.
2001/0029362 A1 10/2001 Sirhan et al.
2001/0044591 A1 11/2001 Stevens et al.
2001/0049547 A1 12/2001 Moore
2002/0029046 A1 3/2002 Lorentzen Cornelius et al.
2002/0045929 A1 4/2002 Diaz
2002/0049412 A1 4/2002 Madrid et al.
2002/0072789 A1 6/2002 Hackett et al.
2002/0107526 A1 8/2002 Greenberg et al.
2002/0111666 A1 8/2002 Hart et al.
2002/0138128 A1 9/2002 Stiger et al.
2002/0156459 A1 10/2002 Ye et al.
2002/0156460 A1 10/2002 Ye et al.
2002/0165523 A1 11/2002 Chin et al.
2002/0188342 A1 12/2002 Rykhus et al.
2003/0004539 A1 1/2003 Linder et al.
2003/0009208 A1 1/2003 Snyder et al.
2003/0050600 A1 3/2003 Ressemann et al.
2003/0191451 A1 10/2003 Gilmartin
2003/0212410 A1 11/2003 Stenzel et al.
2003/0212430 A1 11/2003 Bose et al.
2004/0024416 A1 2/2004 Yodfat et al.
2004/0092879 A1 5/2004 Kraus et al.
2004/0111095 A1 6/2004 Gordon et al.
2004/0143239 A1 7/2004 Zhou et al.
2004/0147903 A1 7/2004 Catini et al.
2004/0158230 A1 8/2004 Hunn et al.

(56) References Cited

U.S. PATENT DOCUMENTS

2004/0181174 A2* 9/2004 Davis ................ A61M 25/0013 600/585
2004/0193140 A1 9/2004 Griffin et al.
2004/0193243 A1 9/2004 Mangiardi et al.
2004/0204749 A1* 10/2004 Gunderson .............. A61F 2/91 623/1.12
2004/0220585 A1 11/2004 Nikolchev
2004/0230285 A1 11/2004 Gifford et al.
2004/0260271 A1 12/2004 Huyser et al.
2004/0260384 A1 12/2004 Allen
2004/0267348 A1 12/2004 Gunderson et al.
2005/0033403 A1 2/2005 Ward et al.
2005/0070794 A1 3/2005 Deal et al.
2005/0090802 A1 4/2005 Connors et al.
2005/0096724 A1 5/2005 Stenzel et al.
2005/0119719 A1 6/2005 Wallace et al.
2005/0125051 A1 6/2005 Eidenschink et al.
2005/0131449 A1 6/2005 Salahieh et al.
2005/0143773 A1 6/2005 Abrams et al.
2005/0149160 A1 7/2005 McFerran et al.
2005/0182388 A1 8/2005 Garabedian et al.
2005/0182475 A1 8/2005 Jen et al.
2005/0228361 A1 10/2005 Tremaglio
2005/0240254 A1 10/2005 Austin
2005/0273149 A1 12/2005 Tran et al.
2005/0277949 A1 12/2005 Que et al.
2006/0030835 A1 2/2006 Sherman et al.
2006/0036309 A1 2/2006 Hebert et al.
2006/0058865 A1 3/2006 Case et al.
2006/0064123 A1 3/2006 Bonnette et al.
2006/0074477 A1 4/2006 Berthiaume et al.
2006/0089618 A1 4/2006 Mcferran et al.
2006/0095050 A1 5/2006 Hartley et al.
2006/0100687 A1 5/2006 Fahey et al.
2006/0100688 A1 5/2006 Jordan et al.
2006/0116750 A1 6/2006 Hebert et al.
2006/0129166 A1 6/2006 Lavelle
2006/0178698 A1 8/2006 McIntyre et al.
2006/0184226 A1 8/2006 Austin
2006/0212042 A1 9/2006 Lamport et al.
2006/0217682 A1 9/2006 Stivland et al.
2006/0235502 A1 10/2006 Belluche et al.
2007/0027520 A1 2/2007 Sherburne
2007/0043430 A1 2/2007 Stinson
2007/0049903 A1 3/2007 Jansen et al.
2007/0078504 A1 4/2007 Mialhe
2007/0088323 A1 4/2007 Campbell et al.
2007/0100421 A1 5/2007 Griffin
2007/0117645 A1 5/2007 Nakashima
2007/0129706 A1 6/2007 Katoh et al.
2007/0149927 A1 6/2007 Itou et al.
2007/0161956 A1 7/2007 Heuser
2007/0185446 A1 8/2007 Accisano
2007/0203563 A1 8/2007 Hebert et al.
2007/0233224 A1 10/2007 Leynov et al.
2007/0239254 A1 10/2007 Chia et al.
2007/0239261 A1 10/2007 Bose et al.
2007/0250039 A1 10/2007 Lobbins et al.
2007/0250040 A1 10/2007 Provost et al.
2007/0255255 A1 11/2007 Shah et al.
2007/0255388 A1 11/2007 Rudakov et al.
2007/0270779 A1 11/2007 Jacobs et al.
2007/0299424 A1 12/2007 Cumming et al.
2007/0299500 A1 12/2007 Hebert et al.
2007/0299501 A1 12/2007 Hebert et al.
2007/0299502 A1 12/2007 Hebert et al.
2008/0009934 A1 1/2008 Schneider et al.
2008/0015558 A1 1/2008 Harlan
2008/0015678 A1 1/2008 Kaplan et al.
2008/0027528 A1 1/2008 Jaooer et al.
2008/0033399 A1 2/2008 Hunn et al.
2008/0033528 A1 2/2008 Satasiva et al.
2008/0051705 A1 2/2008 Von Oepen et al.
2008/0051761 A1 2/2008 Slazas et al.
2008/0071301 A1 3/2008 Matsuura et al.
2008/0077229 A1 3/2008 Andreas et al.
2008/0082083 A1 4/2008 Forde et al.
2008/0091169 A1 4/2008 Heideman et al.
2008/0097398 A1 4/2008 Mitelberg et al.
2008/0108974 A1 5/2008 Yee Roth
2008/0132933 A1 6/2008 Gerber
2008/0140180 A1 6/2008 Dolan et al.
2008/0147001 A1 6/2008 Il-Marashi et al.
2008/0147162 A1 6/2008 Andreas et al.
2008/0177249 A1 7/2008 Heuser et al.
2008/0188865 A1 8/2008 Miller et al.
2008/0188928 A1 8/2008 Salahieh et al.
2008/0221666 A1 9/2008 Icata et al.
2008/0234660 A2 9/2008 Cumming et al.
2008/0234795 A1 9/2008 Snow et al.
2008/0243225 A1 10/2008 Satasiva et al.
2008/0255541 A1 10/2008 Hoffman et al.
2008/0255653 A1 10/2008 Schkolnik
2008/0255654 A1 10/2008 Hebert et al.
2008/0262471 A1 10/2008 Warnock
2008/0262472 A1 10/2008 Lunn et al.
2008/0262592 A1 10/2008 Jordan et al.
2008/0275426 A1 11/2008 Holman et al.
2008/0300667 A1 12/2008 Hebert et al.
2008/0312639 A1 12/2008 Weber
2009/0012500 A1 1/2009 Murata et al.
2009/0082609 A1 3/2009 Condado
2009/0105802 A1 4/2009 Henry et al.
2009/0125053 A1 5/2009 Ferrera et al.
2009/0132019 A1 5/2009 Duffy et al.
2009/0138066 A1 5/2009 Leopold et al.
2009/0143849 A1 6/2009 Ozawa et al.
2009/0149835 A1 6/2009 Velasco et al.
2009/0157048 A1 6/2009 Sutermeister et al.
2009/0160112 A1 6/2009 Ostrovsky
2009/0171319 A1 7/2009 Guo et al.
2009/0204196 A1 8/2009 Weber
2009/0240235 A1 9/2009 Murata
2009/0264985 A1 10/2009 Bruszewski
2009/0287182 A1 11/2009 Bishop et al.
2009/0287183 A1 11/2009 Bishop et al.
2009/0287187 A1 11/2009 Legaspi et al.
2009/0287292 A1 11/2009 Becking et al.
2009/0299333 A1 12/2009 Wendlandt et al.
2009/0299449 A1 12/2009 Styrc
2009/0318947 A1 12/2009 Garcia et al.
2010/0020354 A1 1/2010 Ito
2010/0036363 A1 2/2010 Watanabe et al.
2010/0049293 A1 2/2010 Zukowski et al.
2010/0049297 A1 2/2010 Dorn
2010/0057184 A1 3/2010 Randolph et al.
2010/0057185 A1 3/2010 Melsheimer et al.
2010/0069852 A1 3/2010 Kelley
2010/0087913 A1 4/2010 Rabkin et al.
2010/0094258 A1 4/2010 Shimogami et al.
2010/0094394 A1 4/2010 Beach et al.
2010/0094395 A1 4/2010 Kellett
2010/0100106 A1 4/2010 Ferrera
2010/0160863 A1 6/2010 Heuser
2010/0198334 A1 8/2010 Yodfat et al.
2010/0204770 A1 8/2010 Mas et al.
2010/0217235 A1 8/2010 Thorstenson et al.
2010/0256602 A1 10/2010 Lippert et al.
2010/0256603 A1 10/2010 Lippert et al.
2010/0262157 A1 10/2010 Silver et al.
2010/0268243 A1 10/2010 Parker
2010/0268328 A1 10/2010 Stiger
2010/0274270 A1 10/2010 Patel et al.
2010/0298931 A1 11/2010 Quadri et al.
2010/0331951 A1 12/2010 Bei et al.
2011/0009943 A1 1/2011 Paul et al.
2011/0022157 A1 1/2011 Essinger et al.
2011/0029065 A1 2/2011 Wood et al.
2011/0034987 A1 2/2011 Kennedy
2011/0054586 A1 3/2011 Mayberry et al.
2011/0093055 A1 4/2011 Kujawski
2011/0098804 A1 4/2011 Yeung et al.
2011/0106235 A1 5/2011 Haverkost et al.
2011/0112623 A1 5/2011 Schatz

(56) References Cited

U.S. PATENT DOCUMENTS

2011/0137403 A1 6/2011 Rasmussen et al.
2011/0152760 A1 6/2011 Parker
2011/0160763 A1 6/2011 Ferrera et al.
2011/0178588 A1 7/2011 Haselbv
2011/0190862 A1 8/2011 Bashiri et al.
2011/0190865 A1 8/2011 McHugo et al.
2011/0208292 A1 8/2011 Von Oepen et al.
2011/0224650 A1 9/2011 Itou et al.
2011/0257720 A1 10/2011 Peterson et al.
2011/0288626 A1 11/2011 Straubinger et al.
2011/0319904 A1 12/2011 Hollett et al.
2012/0029607 A1 2/2012 McHugo et al.
2012/0035700 A1 2/2012 Leanna et al.
2012/0053681 A1 3/2012 Alkhatib et al.
2012/0059449 A1 3/2012 Dorn et al.
2012/0065660 A1 3/2012 Ferrera et al.
2012/0116494 A1* 5/2012 Leynov .................... A61F 2/95 623/1.12
2012/0123511 A1 5/2012 Brown
2012/0226343 A1* 9/2012 Vo ............................ A61F 2/95 623/1.12
2012/0253447 A1 10/2012 Hayasaka et al.
2012/0316638 A1 12/2012 Grad et al.
2013/0085562 A1 4/2013 Rincon et al.
2013/0131775 A1 5/2013 Hadley et al.
2013/0172925 A1 7/2013 Garcia et al.
2013/0172979 A1 7/2013 Farqahi
2013/0226276 A1 8/2013 Newell et al.
2013/0226278 A1 8/2013 Newell et al.
2013/0261730 A1 10/2013 Bose et al.
2013/0274618 A1 10/2013 Hou et al.
2013/0274859 A1 10/2013 Argentine
2013/0282099 A1 10/2013 Huynh
2013/0304185 A1 11/2013 Newell et al.
2014/0025150 A1 1/2014 Lim
2014/0031918 A1 1/2014 Newell et al.
2014/0148893 A1 5/2014 Kusleika
2014/0171826 A1 6/2014 Campropoulis et al.
2014/0172067 A1 6/2014 Brown et al.
2014/0194919 A1 7/2014 Losordo et al.
2014/0200648 A1 7/2014 Newell et al.
2014/0277332 A1 9/2014 Slazas et al.
2015/0032198 A1 1/2015 Folk
2015/0066128 A1 3/2015 Losordo et al.
2015/0066129 A1 3/2015 Nageswaran et al.
2015/0066130 A1 3/2015 Haaastrom et al.
2015/0066131 A1 3/2015 Luong et al.
2015/0080937 A1 3/2015 Davidson
2015/0133990 A1 5/2015 Davidson
2015/0164666 A1 6/2015 Johnson et al.
2015/0238336 A1 8/2015 Johnson et al.
2016/0113793 A1* 4/2016 Nishigishi ................. A61F 2/95
2017/0035592 A1 2/2017 Haggstrom
2017/0252161 A1 9/2017 Tran et al.
2018/0200092 A1 7/2018 Nageswaran et al.
2018/0263799 A1 9/2018 Elwood et al.
2019/0314176 A1 10/2019 Nageswaran et al.
2019/0314177 A1 10/2019 Alonso et al.
2019/0314179 A1 10/2019 Nageswaran et al.
2019/0336312 A1 11/2019 Nageswaran et al.
2020/0375769 A1 12/2020 Nageswaran et al.
2020/0405517 A1 12/2020 Barooni

FOREIGN PATENT DOCUMENTS

WO 9820811 A1 5/1998
WO WO-2010/127838 11/2010
WO WO-2011/076408 6/2011
WO 2011081997 A1 7/2011
WO WO-2012/158152 A1 11/2012
WO 2014074462 A2 5/2014

OTHER PUBLICATIONS

Search Report dated Mar. 24, 2020, CN Application No. 201880007614.9, 10 pages.

* cited by examiner

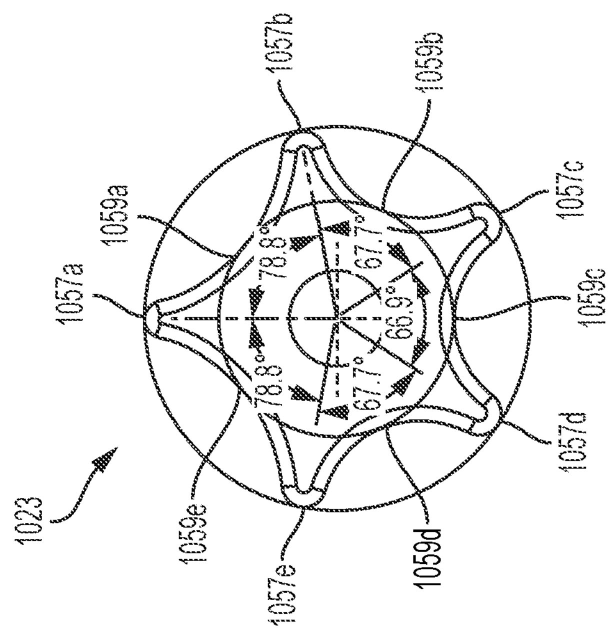
FIG. 10A
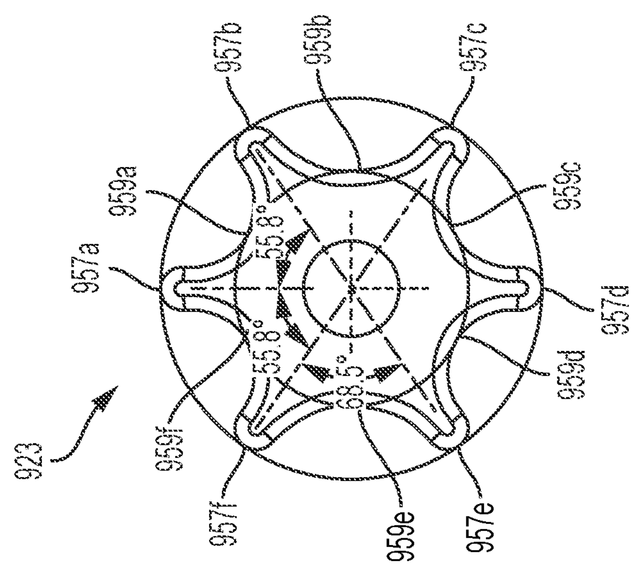
FIG. 9A
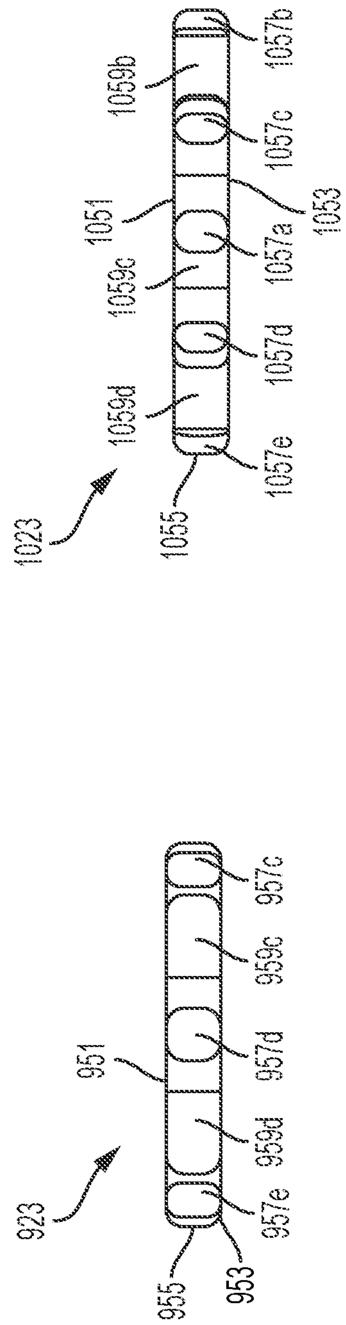
FIG. 10B
FIG. 9B

MEDICAL DEVICE DELIVERY

BACKGROUND

Walls of the vasculature, particularly arterial walls, may develop areas of pathological dilatation called aneurysms that often have thin, weak walls that are prone to rupturing. Aneurysms are generally caused by weakening of the vessel wall due to disease, injury, or a congenital abnormality. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to “fill” an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to support the vessel from collapsing. Methods for delivering these intravascular stents are also well known.

Conventional methods of introducing a compressed stent into a vessel and positioning it within an area of stenosis or an aneurysm include percutaneously advancing a distal portion of a guiding catheter through the vascular system of a patient until the distal portion is proximate the stenosis or aneurysm. A second, inner catheter and a guidewire within the inner catheter are advanced through the distal region of the guiding catheter. The guidewire is then advanced out of the distal region of the guiding catheter into the vessel until the distal portion of the guidewire carrying the compressed stent is positioned at the point of the lesion within the vessel. The compressed stent is then released and expanded so that it supports the vessel at the point of the lesion.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., Clause 1 or Clause 23. The other clauses can be presented in a similar manner.

Clause 1. A stent delivery system, comprising:

a core member configured for advancement within a corporeal lumen;

a stent extending along the core member, the stent characterized by a pore length; and a coupling assembly positioned about the core member, the coupling assembly comprising:

a first plate rotatably coupled to the core member, the first plate including an outer surface having three or more projections engaging the stent; and a second plate rotatably coupled to the core member, the second plate including an outer surface having three or more projections engaging the stent;

wherein the projections of the first plate are spaced longitudinally from the projections of the second plate by a first longitudinal distance that is slightly less than a whole number multiple of the pore length.

Clause 2. The system of any Clause 1, wherein, in a delivery configuration, the projections of the first plate are engaged with pores of the stent at a first longitudinal position, and wherein the projections of the second plate are engaged with pores of the stent at a second longitudinal position, and wherein the first longitudinal position and the second longitudinal position spaced apart by the first longitudinal distance.

Clause 3. The system of any one of Clauses 1-2, wherein the first longitudinal distance is less than two pore lengths.

Clause 4. The system of any one of Clauses 1-3, wherein a projection of the first plate engages a first pore of the stent, a projection of the second plate engages a second pore of the stent, and wherein the first pore and the second pore are longitudinally adjacent.

Clause 5. The system of any one of Clauses 1-4, wherein the projections of the first plate engage the stent at a position less than five pore lengths away from a proximal end of the stent.

Clause 6. The system of any one of Clauses 1-5, wherein the projections of the first plate engage the stent at a position less than three pore lengths away from a proximal end of the stent.

Clause 7. The system of any one of Clauses 1-7, wherein the first plate is configured to tilt with respect to a longitudinal axis of the core member.

Clause 8. The system of Clause 7, wherein the first plate is configured to tilt up to 30 degrees with respect to the longitudinal axis of the core member.

Clause 9. The system of any one of Clauses 7-8, wherein the first plate is configured to tilt up to 20 degrees with respect to the longitudinal axis of the core member.

Clause 10. The system of any one of Clauses 7-9, wherein the first plate is configured to tilt up to 10 degrees with respect to the longitudinal axis of the core member.

Clause 11. The system of any one of Clauses 1-11, wherein the second plate is configured to tilt with respect to a longitudinal axis of the core member.

Clause 12. The system of any Clause 11, wherein the second plate is configured to tilt up to 30 degrees with respect to the longitudinal axis of the core member.

Clause 13. The system of any one of Clauses 11-12, wherein the second plate is configured to tilt up to 20 degrees with respect to the longitudinal axis of the core member.

Clause 14. The system of any one of Clauses 11-13, wherein the second plate is configured to tilt up to 10 degrees with respect to the longitudinal axis of the core member.

Clause 15. The system of any one of Clauses 1-14, wherein the first longitudinal distance is less than a whole number multiple of the pore length by a decrement that is equal to 1% to 50% of the pore length.

Clause 16. The system of any one of Clauses 1-15, wherein the first longitudinal distance is less than a whole number multiple of the pore length by a decrement that is equal to 1% to 40% of the pore length.

Clause 17. The system of any one of Clauses 1-16, wherein the first longitudinal distance is less than a whole number multiple of the pore length by a decrement that is equal to 1% to 30% of the pore length.

Clause 18. The system of any one of Clauses 1-17, wherein the first longitudinal distance is less than a whole number multiple of the pore length by a decrement that is equal to 1% to 20% of the pore length.

Clause 19. The system of any one of Clauses 1-18, wherein the first longitudinal distance is less than a whole number multiple of the pore length by a decrement that is equal to 1% to 10% of the pore length.

Clause 20. The system of any one of Clauses 1-19, wherein the first longitudinal distance is less than a whole number multiple of the pore length by a decrement that is equal to 1% to 5% of the pore length.

Clause 21. The system of any one of Clauses 1-20, wherein the coupling assembly further comprises a spacer between the first plate and the second plate, and the spacer maintains the projections of the first plate and the second plate at the first longitudinal distance when the core member is in a straight orientation and the first plate and the second plate abut the spacer.

Clause 22. The system of any one of Clauses 1-21, wherein the projections of the first plate and the second plate engage the stent by projecting into pores of the stent.

Clause 23. The system of any one of Clauses 1-22, wherein the pore length of the stent is that attained when the outer diameter of the stent is equal to the inner diameter of a catheter that contains the stent and the coupling assembly and maintains engagement of the first and second plates and the stent.

Clause 24. The system of any one of Clauses 1-23, wherein:

the stent is a braided stent comprising braided filaments;

a projection of the first plate projects into a first pore of the stent;

a projection of the second plate projects into a second pore of the stent;

the first and second pores are longitudinally adjacent and separated by a filament crossing located longitudinally between the first pore and the second pore;

the projection of the first plate is longitudinally offset from a center of the first pore, in a direction toward the filament crossing; and the projection of the second plate is longitudinally offset from a center of the second pore, in a direction toward the filament crossing and the projection of the first plate.

Clause 25. The system of any one of Clauses 1-24, further comprising a proximal restraint carried by the core member, wherein the coupling assembly is positioned distal of the proximal restraint.

Clause 26. A stent delivery system, comprising:

a core member;

a stent extending along the core member, the stent comprising a plurality of pores and being characterized by a pore length; and a coupling assembly carried by the core member; the coupling assembly comprising:

a first stent engagement member rotatably coupled to the core member, the first stent engagement member including projections engaging a first plurality of pores of the stent;

a second stent engagement member rotatably coupled to the core member, the second stent engagement member including projections engaging a second plurality of pores of the stent, wherein the projections of the first stent engagement member are spaced longitudinally from the projections of the second stent engagement member by a first longitudinal distance that is slightly less than a whole number multiple of the pore length.

Clause 27. The system of Clause 26, wherein the first plurality of pores and the second plurality of pores are longitudinally adjacent along a length of the stent.

Clause 28. The system of any one of Clauses 26-27, wherein the first plurality of pores are less than five pore lengths away from a proximal end of the stent.

Clause 29. The system of any one of Clauses 26-28, wherein the first plurality of pores are less than three pore lengths away from a proximal end of the stent.

Clause 30. The system of any one of Clauses 26-29, wherein the first engagement member is configured to tilt with respect to a longitudinal axis of the core member.

Clause 31. The system of Clause 30, wherein the first engagement member is configured to tilt up to 30 degrees with respect to the longitudinal axis of the core member.

Clause 32. The system of any one of Clauses 30-31, wherein the first engagement member is configured to tilt up to 20 degrees with respect to the longitudinal axis of the core member.

Clause 33. The system of any one of Clauses 30-32, wherein the first engagement member is configured to tilt up to 10 degrees with respect to the longitudinal axis of the core member.

Clause 34. The system of any one of Clauses 26-33, wherein the second engagement member is configured to tilt with respect to a longitudinal axis of the core member.

Clause 35. The system of Clause 34, wherein the second engagement member is configured to up to 30 degrees with respect to the longitudinal axis of the core member.

Clause 36. The system of any one of Clauses 34-35, wherein the second engagement member is configured to tilt up to 20 degrees with respect to the longitudinal axis of the core member.

Clause 37. The system of any one of Clauses 34-36, wherein the second engagement member is configured to tilt up to 10 degrees with respect to the longitudinal axis of the core member.

Clause 38. The system of any one of Clauses 26-37, wherein the first stent engagement member and the second stent engagement member are spaced apart by less than two pore lengths.

Clause 39. The system of any one of Clauses 26-38, wherein the first longitudinal distance is less than a whole number multiple of the pore length by a decrement that is equal to 1% to 50% of the pore length.

Clause 40. The system of any one of Clauses 26-39, wherein the first longitudinal distance is less than a whole number multiple of the pore length by a decrement that is equal to 1% to 40% of the pore length.

Clause 41. The system of any one of Clauses 26-40, wherein the first longitudinal distance is less than a whole number multiple of the pore length by a decrement that is equal to 1% to 30% of the pore length.

Clause 42. The system of any one of Clauses 26-41, wherein the first longitudinal distance is less than a whole number multiple of the pore length by a decrement that is equal to 1% to 20% of the pore length.

Clause 43. The system of any one of Clauses 26-42, wherein the first longitudinal distance is less than a whole number multiple of the pore length by a decrement that is equal to 1% to 10% of the pore length.

Clause 44. The system of any one of Clauses 26-43, wherein the first longitudinal distance is less than a whole number multiple of the pore length by a decrement that is equal to 1% to 5% of the pore length.

Clause 45. The system of any one of Clauses 26-44, wherein the coupling assembly further comprises a spacer between the first engagement member and the second engagement member, and the spacer maintains the projections of the first engagement member and the second engagement member at the first longitudinal distance when the core member is in a straight orientation and the first engagement member and the second engagement member abut the spacer.

Clause 46. The system of any one of Clauses 26-45, wherein the projections of the first engagement member and the second engagement member engage the stent by projecting into pores of the stent.

Clause 47. The system of any one of Clauses 26-46, wherein the pore length of the stent is that attained when the outer diameter of the stent is equal to the inner diameter of a catheter that contains the stent and the coupling assembly and maintains engagement of the first and second engagement members and the stent.

Clause 48. The system of any one of Clauses 26-47, wherein:

the stent is a braided stent comprising braided filaments;

a projection of the first engagement member projects into a first pore of the stent;

a projection of the second engagement member projects into a second pore of the stent;

the first and second pores are longitudinally adjacent and separated by a filament crossing located longitudinally between the first pore and the second pore;

the projection of the first engagement member is longitudinally offset from a center of the first pore, in a direction toward the filament crossing; and the projection of the second engagement member is longitudinally offset from a center of the second pore, in a direction toward the filament crossing and the projection of the first engagement member.

Clause 49. The system of any one of Clauses 26-48, further comprising a proximal restraint carried by the core member, wherein the coupling assembly is positioned distal of the proximal restraint.

Clause 50. A method of advancing a stent within a catheter, the method comprising:

moving a core member distally within a lumen of the catheter, the core member carrying a coupling assembly engaged with at least a portion of the stent, the coupling assembly including:

a first stent engagement member rotatably carried by the core member and comprising projections engaged with the stent; and a second stent engagement member rotatably carried by the core member and comprising projections engaged with the stent;

wherein the stent is characterized by a pore length; and wherein the projections of the first stent engagement member are spaced longitudinally from the projections of the second stent engagement member;

by moving the core member distally, causing the stent to move distally within the catheter lumen with the first engagement member moving no more than a first lag distance relative to the stent before initiating distal movement of the stent;

wherein the first lag distance is no more than 40% of the pore length.

Clause 51. The method of Clause 50, wherein, after distally advancing the core member such that a portion of the stent is permitted to extend out of the catheter and expand, a proximal portion of the stent remains engaged with the first stent engagement member.

Clause 52. The method of Clause 51, further comprising proximally retracting the core member prior to releasing the stent such that the stent is recaptured to within the catheter lumen.

Clause 53. The method of Clause 52, wherein by proximally retracting the core member, the first stent engagement member pulls the stent proximally within the catheter lumen.

Clause 54. The method of any one of Clauses 52-53, wherein the portion of the stent expanded prior to recapture is at least 50% of the length of the stent.

Clause 55. The method of any one of Clauses 52-54, wherein the portion of the stent expanded prior to recapture is at least 75% of the length of the stent.

Clause 56. The method of any one of Clauses 52-55, wherein the portion of the stent expanded prior to recapture is at least 90% of the length of the stent.

Clause 57. The method of any one of Clauses 52-56, wherein the moving comprises causing the stent to rotate with respect to the core member.

Clause 58. The method of any one of Clauses 52-57, further comprising by proximally retracting the core member, causing the stent to move proximally within the catheter lumen with the first engagement member moving no more than a second lag distance relative to the stent before initiating proximal movement of the stent, wherein the second lag distance is no more than 40% of the pore length.

Clause 59. The method of any one of Clauses 50-58, wherein the projections of the first stent engagement member are spaced longitudinally from the projections of the second stent engagement member by a first longitudinal distance that is slightly less than a whole number multiple of the pore length.

Clause 60. The method of any one of Clauses 50-59, wherein the first lag distance is no more than 33% of the pore length.

Clause 61. The method of any one of Clauses 50-60, wherein the first lag distance is no more than 25% of the pore length.

Clause 62. The method of any one of Clauses 50-61, wherein the first lag distance is no more than 20% of the pore length.

Clause 63. The method of any one of Clauses 50-62, wherein the first lag distance is no more than 15% of the pore length.

Clause 64. The method of any one of Clauses 50-63, wherein the first lag distance is no more than 10% of the pore length.

Clause 65. The method of any one of Clauses 50-64, wherein the first lag distance is no more than 5% of the pore length.

Clause 66. A stent delivery system, comprising:

a core member configured for advancement within a corporeal lumen;

a stent engagement member coupled to the core member, the engagement member including:

a proximal end face;

a distal end face;

a side surface extending between the proximal end face and the distal end face, the side surface comprising three or more projections separated by recesses, wherein the projections are unevenly spaced apart from one another along the side surface; and an aperture extending through the proximal end face and second end faces, the core member extending through the aperture such that the engagement member can rotate about the core member; and a stent extending along the core member and over the engagement member.

Clause 67. The stent delivery system of Clause 66, wherein the projections are spaced apart such that each projection is substantially aligned with a pore of the stent when the stent is engaged with the engagement member.

Clause 68. The stent delivery system of any one of Clauses 66-17, wherein the stent comprises a braided stent having 48, 54, or 64 wires.

Clause 69. The stent delivery system of any one of Clauses 66-68, wherein the stent comprises a number of pores around its circumference at a given longitudinal position along the stent, and wherein the number of pores is not evenly divisible by the number of projections of the engagement member.

Clause 70. The stent delivery system of Clause 69, wherein the stent comprises 32 pores at a first longitudinal position along the stent, and wherein the stent engagement member has 3, 5, 6, or 7 projections.

Clause 71. The stent delivery system of any one of Clauses 69-70, wherein the stent comprises 24 pores at a first longitudinal position along the stent, and wherein the stent engagement member has 5, 7, or 9 projections.

Clause 72. The stent delivery system of any one of Clauses 69-71, wherein the stent comprises 27 pores at a first longitudinal position along the stent, and wherein the stent engagement member has 4, 5, 6, 7, or 8 projections.

Clause 73. The stent delivery system of any one of Clauses 66-72, wherein the recesses each comprise a concave portion having a radius of curvature, and wherein the radius of curvature of the concave portions varies among the plurality of recesses.

Clause 74. The stent delivery system of any one of Clauses 66-73, wherein the recesses each comprise a concave portion having a surface area, and wherein the surface area of the concave portions varies among the plurality of recesses.

Clause 75. The stent delivery system of any one of Clauses 66-74, wherein the recesses each have an angular size, and the recesses vary in angular size.

Clause 76. The stent delivery system of any one of Clauses 66-75, wherein the engagement member comprises a first edge formed at the intersection of the proximal end face and the side surface, and a second edge formed at the intersection of the distal end face and the side surface, and wherein the first edge and the second edge are rounded.

Clause 77. The stent delivery system of any one of Clauses 66-76, wherein the projections each comprise a radially outermost contact region configured to engage the stent.

Clause 78. The stent delivery system of Clause 77, wherein each contact region includes:

a central portion;

a first shoulder portion extending from the central portion towards a first adjacent recess; and a second shoulder portion extending from the central portion towards a second adjacent recess.

Clause 79. The stent delivery system of Clause 78, wherein the central portion comprises a substantially planar outer surface.

Clause 80. The stent delivery system of any one of Clauses 66-79, wherein the projections each comprise a radially outermost contact region configured to interlock with the stent.

Clause 81. The stent delivery system of any one of Clauses 66-80, wherein the projections each comprise a radially outermost contact region configured to project into one or more pores of the stent.

Clause 82. The stent delivery system of any one of Clauses 66-81, further comprising a catheter having an inner surface and a lumen through which the core member extends, wherein at least a portion of the stent is radially positioned between the engagement member side surface and the catheter inner surface.

Clause 83. The stent delivery system of any one of Clauses 66-82, wherein the engagement member has a thickness of between about 50-100 microns.

Clause 84. The stent delivery system of any one of Clauses 66-83, wherein the number of protrusions of is between three and six.

Clause 85. The stent delivery system of any one of Clauses 66-84, wherein the stent engagement member comprises a rigid plate.

Clause 86. The stent delivery system of any one of Clauses 66-85, wherein the stent engagement member comprises a sprocket.

Clause 87. The stent delivery system of any one of Clauses 66-86, wherein a radially largest dimension of the stent engagement member is at least five times greater than a thickness of the stent engagement member.

Clause 88. The stent delivery system of any one of Clauses 66-87, wherein the aperture is configured such that the engagement member can tilt with respect to a longitudinal axis of the core member.

Clause 89. The stent delivery system of any Clause 88, wherein the engagement member can tilt up to 30 degrees with respect to the longitudinal axis of the core member.

Clause 90. The stent delivery system of any one of Clauses 88-89, wherein the engagement member can tilt up to 20 degrees with respect to the longitudinal axis of the core member.

Clause 91. The stent delivery system of any one of Clauses 88-90, wherein the engagement member can tilt up to 10 degrees with respect to the longitudinal axis of the core member.

Clause 92. A stent engagement member for a stent delivery system, the engagement member comprising:

a first end face;

a second end face opposite the first end face;

a side surface extending between the proximal end face and the distal end face, the side surface comprising three or more projections separated by recesses, wherein the projections are unevenly spaced apart from one another along the side surface; and a central opening extending through the proximal end face and second end faces, the opening configured to receive a core member therethrough.

Clause 93. The stent engagement member of Clause 92, wherein the recesses each comprise a concave portion having a radius of curvature, and wherein the radius of curvature of the concave portions varies among the plurality of recesses.

Clause 94. The stent delivery system of any one of Clauses 92-93, wherein the recesses each have an angular size, and the recesses vary in angular size.

Clause 95. The stent engagement member of any one of Clauses 92-94, wherein the recesses each comprise a concave portion having a surface area, and wherein the surface area of the concave portions varies among the plurality of recesses.

Clause 96. The engagement member system of any one of Clauses 92-95, wherein the engagement member comprises a first edge between the proximal end face and the side surface, and a second edge between the distal end face and the side surface, and wherein the first edge and the second edge are rounded.

Clause 97. The stent engagement member of any one of Clauses 92-96, wherein the projections each comprise a radially outermost contact region, wherein each contact region includes:

a central portion;

a first shoulder portion extending from the central portion towards a first adjacent recess; and a second shoulder portion extending from the central portion towards a second adjacent recess.

Clause 98. The stent engagement member of Clause 97, wherein the central portion comprises a generally flat outer surface.

Clause 99. The stent engagement member of any one of Clauses 92-98, wherein the engagement member has a thickness of between about 50-100 microns.

Clause 100. The stent engagement member of any one of Clauses 92-99, wherein the number of protrusions of is between three and six.

Clause 101. The stent engagement member of any one of Clauses 92-100, wherein the stent engagement member comprises a rigid plate.

Clause 102. The stent engagement member of any one of Clauses 92-101, wherein the stent engagement member comprises a sprocket.

Clause 103. The stent engagement member of any one of Clauses 92-102, wherein a radially largest dimension of the stent engagement member is at least five times greater than a thickness of the stent engagement member.

Clause 104. The stent engagement member of any one of Clauses 92-103, wherein the aperture is configured such that the engagement member can tilt with respect to a longitudinal axis of the core member.

Clause 105. A method of advancing a stent delivery assembly through a catheter, the method comprising:

moving a core member distally within a lumen of the catheter, the core member carrying an engagement member engaged with at least a portion of a stent, the engagement member including:

a proximal end face, a distal end face, and a side surface extending between the proximal end face and the distal end face, the side surface comprising three or more projections separated by recesses, wherein the projections are unevenly spaced apart from one another along the side surface, and wherein the projections are in contact with an inner surface of the stent; and an aperture extending through the proximal end face and second end faces, the core member extending through the aperture;

by moving the core member, pulling the stent distally within the catheter lumen; and distally advancing the core member such that a portion of the stent carried by the core member is permitted to extend out of the catheter and expand.

Clause 106. The method of any Clause 105, wherein, after distally advancing the core member such that a portion of the stent is permitted to extend out of the catheter and expand, a proximal portion of the stent remains engaged with the stent engagement member.

Clause 107. The method of any one of Clauses 105-106, further comprising proximally retracting the core member prior to releasing the stent such that the stent is recaptured to within the catheter lumen.

Clause 108. The method of Clause 107, wherein by proximally retracting the core member, the stet engagement member pulls the stent proximally within the catheter lumen.

Clause 109. The method of Clause 108, wherein the portion of the stent expanded prior to recapture is at least 50% of the length of the stent.

Clause 110. The method of any one of Clauses 108-19, wherein the portion of the stent expanded prior to recapture is at least 75% of the length of the stent.

Clause 111. The method of any one of Clauses 108-110, wherein the portion of the stent expanded prior to recapture is at least 90% of the length of the stent.

Clause 112. The method of any one of Clauses 108-111, wherein the moving comprises causing the stent to rotate with respect to the core member.

Clause 113. A stent delivery system comprising:

a core member configured for advancement within a corporeal lumen;

a coupling assembly positioned about the core member, the coupling assembly comprising:

a first plate rotatably positioned about the core member, the first plate including an outer surface having three or more projections separated by recesses;

a pushing element positioned on the core member proximal of the first plate, the pushing element having a distal-facing engagement surface; and a stent extending along the core member such that the stent is engaged by one or more projections of the first plate, the stent having a proximal edge;

wherein the distal-facing engagement surface of the pushing element abuts the proximal edge of the stent.

Clause 114. The system of any Clause 113, wherein the pushing element is configured to transmit distally directed force to the stent but not proximally directed force.

Clause 115. The system of any one of Clauses 113-114, wherein the coupling assembly is configured so that the first plate transmits proximally directed force to the stent but little or no distally directed force.

Clause 116. The system of any one of Clauses 113-115, wherein the coupling assembly further comprises a rigid first spacer situated between the first plate and the pushing element.

Clause 117. The system of Clause 116, wherein the first spacer comprises a solid tube of metal or rigid polymer.

Clause 118. The system of Clause 117, wherein the first spacer lacks flexibility-enhancing cuts.

Clause 119. The system of any one of Clauses 113-118, wherein the first spacer comprises a proximal end face, a distal end face, and an outer surface extending between the proximal end face and the distal end face along a longitudinal axis, and wherein the proximal end face and the distal end face are each substantially orthogonal to the longitudinal axis of the first spacer.

Clause 120. The system of any one of Clauses 113-119, wherein the first spacer comprises a flattened proximal end face configured to abut against the pushing element.

Clause 121. The system of any one of Clauses 113-120, wherein the stent forms a plurality of openings and the projections of the first plate engage the stent by extending into the openings.

Clause 122. The system of any one of Clauses 113-121, wherein the coupling assembly further comprises a second plate rotatably positioned about the core member, the second plate including an outer surface having three or more projections separated by recesses, and wherein one or more of the projections of the second plate engages the stent via openings formed in the stent.

Clause 123. The system of any one of Clauses 113-122, further comprising a sheath or catheter, wherein the core member, coupling assembly and stent are located within the sheath or catheter.

Clause 124. The system of any one of Clauses 113-123, wherein the pushing element comprises a proximal restraining member.

Clause 125. A medical device delivery system, comprising:

a core member;

a coupling assembly carried by the core member, the coupling assembly comprising:

a first device engagement member rotatably coupled to the core member, the first device engagement member including an outer surface having projections separated by recesses; and a pushing element positioned on the core member proximal of the first device engagement member, the pushing element having a distal-facing engagement surface.

Clause 126. The system of Clause 125, further comprising:

a medical device extending along the core member such that the medical device is engaged by one or more projections of the first plate;

wherein the medical device has a proximal edge;

wherein the distal-facing engagement surface of the pushing element abuts the proximal edge of the medical device.

Clause 127. The system of Clause 126, wherein the pushing element is configured to transmit distally directed force to the medical device but not proximally directed force.

Clause 128. The system of any one of Clauses 126-127, wherein the coupling assembly is configured so that the first device engagement member transmits proximally directed force to the medical device but little or no distally directed force.

Clause 129. The system of any one of Clauses 125-128, wherein the coupling assembly further comprises a rigid first spacer situated between the first device engagement member and the pushing element.

Clause 130. The system of Clause 129, wherein the first spacer comprises a solid tube of metal or rigid polymer.

Clause 131. The system of Clause 130, wherein the first spacer lacks flexibility-enhancing cuts.

Clause 132. The system of any one of Clauses 126-131, wherein the medical device forms a plurality of openings and the projections of the first device engagement member engage the medical device by extending into the openings.

Clause 133. The system of Clause 132, wherein the coupling assembly further comprises a second device engagement member rotatably positioned about the core member, the second device engagement member including an outer surface having three or more projections separated by recesses, and wherein one or more of the projections of the second device engagement member engages the medical device via openings formed in the medical device.

Clause 134. The system of any one of Clauses 126-133, further comprising a sheath or catheter, wherein the core member, coupling assembly and medical device are located within the sheath or catheter.

Clause 135. The system of any one of Clauses 125-134, wherein the first device engagement member takes the form of a plate or sprocket.

Clause 136. A method of delivering a tubular medical device through a catheter, the method comprising:

manipulating a delivery system comprising a core member and a coupling assembly, the coupling assembly comprising:

a first device engagement member including an outer surface having projections separated by recesses, the projections engaging the medical device via openings in the medical device; and a pushing element located on the core member, proximal of the first device engagement member; and moving the medical device distally by transmitting distally-directed force to the medical device via the pushing element, and no distally-directed force to the medical device via the first device engagement member.

Clause 137. The method of Clause 136, further comprising moving the medical device proximally by transmitting proximally-directed force to the stent via the first device engagement member, and no proximally-directed force to the stent via the pushing element.

Clause 138. The method of Clause 137, wherein moving the medical device proximally comprises resheathing the medical device.

Clause 139. The method of any one of Clauses 137-138, wherein moving the medical device distally comprises partially expanding the medical device from the end of a catheter or sheath, and moving the medical device proximally comprises resheathing the medical device into the catheter or sheath.

Clause 140. The method of any one of Clauses 136-39, wherein the coupling assembly further comprises a first spacer located on the core member between the first device engagement member and the pushing element.

Clause 141. The method of Clause 140, further comprising maintaining engagement between the medical device and the pushing element via the first spacer.

Clause 142. The method of any one of Clauses 136-141, wherein the medical device comprises a stent.

Clause 143. The method of any one of Clauses 136-142, wherein the first device engagement member takes the form of a plate or sprocket.

Clause 144. A stent delivery system comprising:

a core member configured for advancement within a corporeal lumen;

a coupling assembly positioned about the core member, the coupling assembly comprising:

a first plate rotatably positioned about the core member, the first plate including an outer surface having three or more projections separated by recesses;

a coil spacer positioned about the core member proximal of and adjacent to the first plate; and a stent extending along the core member such that the stent is engaged by one or more projections of the first plate and is thereby distally advanceable via the core member.

Clause 145. The system of Clause 144, wherein the coil spacer comprises a zero-pitch coil.

Clause 146. The system of any one of Clauses 144-145, wherein the coil spacer is axially substantially incompressible.

Clause 147. The system of any one of Clauses 144-146, wherein the coil spacer is rotatably positioned about the core member.

Clause 148. The system of any one of Clauses 144-147, wherein the coil spacer comprises a proximal end face, a distal end face, and an outer surface extending between the proximal end face and the distal end face along a longitudinal axis, and wherein the proximal end face and the distal end face are each substantially orthogonal to the longitudinal axis of the coil spacer.

Clause 149. The system of any one of Clauses 144-148, further comprising a proximal restraint coupled to the core member, and wherein the coil spacer comprises a flattened proximal end face configured to abut against the proximal restraint.

Clause 150. The system of any one of Clauses 144-149, wherein the coil spacer comprises a flattened distal end face configured to abut against the first plate.

Clause 151. The system of any one of Clauses 144-150, wherein the coil spacer has a length of between about 1-2 mm.

Clause 152. The system of any one of Clauses 144-151, wherein the coil spacer is coated with a lubricious material.

Clause 153. The system of Clause 152, wherein the lubricious material comprises PTFE.

Clause 154. The system of any one of Clauses 144-153, wherein an outer diameter of the coil spacer is less than or equal to a recess diameter of the first plate.

Clause 155. The system of any one of Clauses 144-154, wherein a largest radial dimension of the first plate a is configured to fit within a 0.017", 0.021" or 0.027" inner diameter catheter.

Clause 156. The system of any one of Clauses 144-155, wherein the coil spacer comprises a wire having a square or rectangular cross section that is wound into a coil configuration.

Clause 157. The system of any one of Clauses 144-156, wherein the coil spacer comprises a wire that is wound into a coil configuration and the wound wire forms a number of winds, each with flat distal and proximal faces, wherein the faces of adjacent winds contact each other to enable the coil spacer to bear longitudinally compressive loads without shortening.

Clause 158. The system of any one of Clauses 144-157, further comprising a proximal restraint coupled to the core member proximal of and adjacent to the coil spacer so as to prevent longitudinal movement of the coil spacer proximal of the proximal restraint.

Clause 159. The system of any one of Clauses 144-158, wherein the coupling assembly further comprises a second plate rotatably positioned about the core member, the second plate including an outer surface having three or more projections separated by recesses, and wherein one or more of the projections of the second plate engages the stent such that the stent is distally advanceable via the core member.

Clause 160. The system of Clause 159, further comprising a distal restraint disposed distal to the second plate, the distal restraint being longitudinally fixed with respect to the core member.

Clause 161. The system of any one of Clauses 159-160, wherein a largest radial dimension of the first plate is at least 5 times greater than a largest width dimension of the first plate, and wherein a largest radial dimension of the second plate is at least 5 times greater than a largest width dimension of the second plate.

Clause 162. The system of any one of Clauses 159-161, wherein the coupling assembly further comprises a second spacer positioned about the core member and disposed between the first plate and the second plate.

Clause 163. The system of Clause 162, wherein the second spacer comprises a second coil spacer.

Clause 164. The system of any one of Clauses 162-163, wherein the second spacer comprises a solid tubular member.

Clause 165. The system of any one of Clauses 144-164, wherein the coupling assembly is rotatably positioned about the core member.

Clause 166. A medical device delivery system, comprising:

a core member;

a coupling assembly carried by the core member, the coupling assembly comprising:

a first device engagement member rotatably coupled to the core member, the first device engagement member including an outer surface having projections separated by recesses; and a coil spacer coupled to the core member and disposed proximal of and adjacent to the first device engagement member.

Clause 167. The system of Clause 166, wherein the coil spacer comprises a zero-pitch coil.

Clause 168. The system of any one of Clauses 166-167, wherein the coil spacer is axially substantially incompressible.

Clause 169. The system of any one of Clauses 166-168, wherein the coil spacer is rotatably coupled to the core member.

Clause 170. The system of any one of Clauses 166-169, wherein the coil spacer comprises a proximal end face, a distal end face, and an outer surface extending between the proximal end face and the distal end face along a longitudinal axis, and wherein the proximal end face and the distal end face are each substantially planar and orthogonal to the longitudinal axis of the coil spacer.

Clause 171. The system of any one of Clauses 166-170, wherein the coil spacer comprises a flattened proximal end face configured to abut against a proximal restraint coupled to the core member.

Clause 172. The system of any one of Clauses 166-171, wherein the coil spacer comprises a flattened distal end face configured to abut against the first device engagement member.

Clause 173. The system of any one of Clauses 166-172, wherein the coil spacer has a length of between about 1-2 mm.

Clause 174. The system of any one of Clauses 166-173, wherein the coil spacer is coated with a lubricious material.

Clause 175. The system of Clause 174, wherein the lubricious material comprises PTFE.

Clause 176. The system of any one of Clauses 166-175, wherein an outer diameter of the coil spacer is less than or equal to a recess diameter of the first device engagement member.

Clause 177. The system of any one of Clauses 166-176, wherein the first device engagement member comprises a rigid plate or sprocket.

Clause 178. The system of Clause 177, wherein the coupling assembly further comprises a second device engagement member which comprises a rigid plate or sprocket.

Clause 179. The system of any one of Clauses 166-178, wherein the coil spacer comprises a wire having a square or rectangular cross section that is wound into a coil configuration.

Clause 180. The system of any one of Clauses 166-179, wherein the coil spacer comprises a wire that is wound into a coil configuration and the wound wire forms a number of winds, each with flat distal and proximal faces, wherein the faces of adjacent winds contact each other to enable the coil spacer to bear longitudinally compressive loads without shortening.

Clause 181. The system of any one of Clauses 166-180, further comprising a proximal restraint coupled to the core member proximal of and adjacent to the coil spacer so as to prevent longitudinal movement of the coil spacer proximal of the proximal restraint.

Clause 182. The system of any one of Clauses 166-181, wherein the coupling assembly further comprises a second device engagement member rotatably positioned about the core member, the second device engagement member including an outer surface having three or more projections separated by recesses.

Clause 183. The system of Clause 182, further comprising a distal restraint disposed distal to the second device engagement member, the distal restraint being longitudinally fixed with respect to the core member.

Clause 184. The system of any one of Clauses 182-183, wherein a largest radial dimension of the first device engagement member is at least 5 times greater than a largest width dimension of the first device engagement member, and wherein a largest radial dimension of the second device engagement member is at least 5 times greater than a largest width dimension of the second device engagement member.

Clause 185. The system of any one of Clauses 182-184, further comprising an expandable medical device extending along the core member such that the medical device is engaged by one or more projections of the first device engagement member and of the second device engagement member, and is thereby distally advanceable via the core member.

Clause 186. The system of Clause 185, wherein the medical device comprises a stent.

Clause 187. The system of any one of Clauses 182-186, wherein the coupling assembly further comprises a second spacer positioned about the core member and disposed between the first device engagement member and the second device engagement member.

Clause 188. The system of Clause 187, wherein the second spacer comprises a second coil spacer.

Clause 189. The system of Clause 187, wherein the second spacer comprises a solid tubular member.

Clause 190. The system of any one of Clauses 166-189 wherein the coupling assembly is rotatably positioned about the core member.

Clause 191. The system of any one of Clauses 166-190, wherein the core member is configured for advancement within a corporeal lumen.

Clause 192. A method of advancing a medical device within a catheter, the method comprising:

moving a core member distally within a lumen of the catheter, the core member carrying a coupling assembly engaged with at least a portion of the medical device within the catheter, the coupling assembly including:

a first device engagement member rotatably carried by the core member and comprising projections engaged with the medical device; and a coil spacer carried by the core member and positioned proximal of the first device engagement member;

by moving the core member distally, causing the medical device to move distally within the catheter; and while moving the core member distally, transmitting distally-directed force from the core member to the first device engagement member and the medical device via the coil spacer, without longitudinal shortening of the coil spacer.

Clause 193. The method Clause 192, wherein the medical device comprises a stent.

Clause 194. The method of any one of Clauses 192-193, wherein moving the medical device distally further comprises causing the medical device to extend out of the catheter and expand.

Clause 195. The method of Clause 194, further comprising proximally retracting the core member prior to releasing the medical device such that the device is recaptured to within the catheter lumen.

Clause 196. The method of any one of Clauses 193-195, wherein, as a result of proximally retracting the core member, the first device engagement member pulls the stent proximally within the catheter lumen.

Clause 197. The method of any one of Clauses 195-196, wherein the portion of the medical device expanded prior to recapture is at least 50% of the length of the device.

Clause 198. The method of any one of Clauses 195-197, wherein the portion of the medical device expanded prior to recapture is at least 75% of the length of the device.

Clause 199. The method of any one of Clauses 195-198, wherein the portion of the medical device expanded prior to recapture is at least 90% of the length of the device.

Clause 200. The method of any one of Clauses 192-199, wherein the moving comprises causing the medical device to rotate with respect to the core member.

Clause 201. The method of any one of Clauses 192-200, further comprising advancing the core member and coil spacer through a bend in the catheter, and thereby bending the coil spacer.

Clause 202. The method of Clause 201, wherein bending the coil spacer comprises bending the coil spacer while transmitting distally-directed force from the core member to the first device engagement member and the medical device via the coil spacer.

Clause 203. The method of any one of Clauses 192-202, wherein the coupling assembly further comprises a second device engagement member rotatably carried by the core member and comprising projections engaged with the medical device.

Clause 204. The method of Clause 203, further comprising while moving the core member distally, transmitting distally-directed force from the core member to the second device engagement member and the medical device via the coil spacer.

Clause 205. The method of any one of Clauses 203-204, wherein the coupling assembly further comprises a second spacer carried by the core member and located between the first device engagement member and the second device engagement member.

Clause 206. The method of any one of Clauses 192-205, wherein the medical device comprises a flow-diverting stent, and further comprising deploying the stent from the catheter across an aneurysm to treat the aneurysm via flow diversion therapy.

Additional features and advantages of the present technology will be set forth in the description below, and in part will be apparent from the description, or may be learned by practice of the subject technology. The advantages of the present technology will be realized and attained by the structure particularly pointed out in the written description and claims hereof as well as the appended drawings.

It is to be understood that both the foregoing general description and the following detailed description are exemplary and explanatory and are intended to provide further explanation of the present technology as claimed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 9A and 9B are side and bottom views, respectively, of another embodiment of a stent engagement member.

FIGS. 10A and 10B are side and bottom views, respectively, of another embodiment of a stent engagement member.

DETAILED DESCRIPTION

Figure 1:
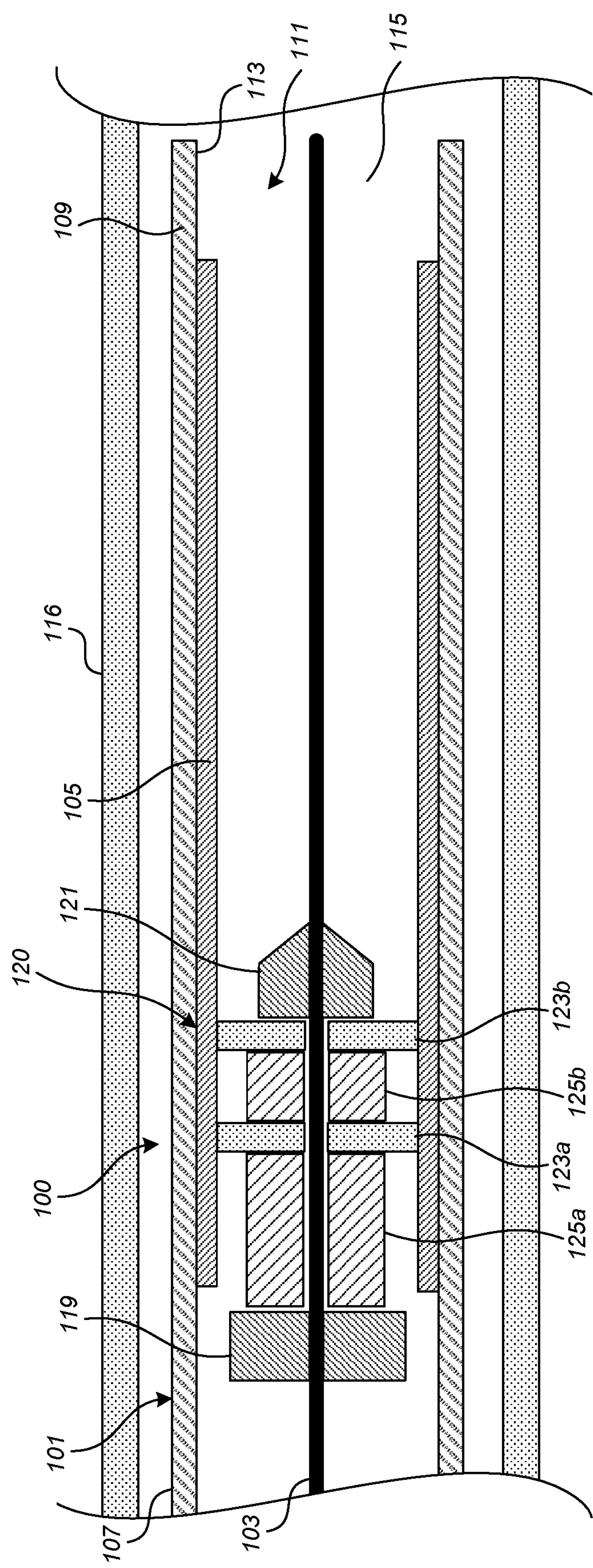
FIG. 1 is a schematic illustration of a medical device delivery system configured in accordance with some embodiments.

Conventional stent engagement members include soft "pads" that rely on friction fit to secure a stent (such as a braided, knit or woven stent, or a laser-cut stent, or other tubular implant or medical device) against an inner wall of a catheter. Such friction-fit pads may require several different pad diameters to accommodate different stent sidewall thicknesses, which can vary based on the wire size (or combinations of wire sizes), or the sidewall thickness of the tube stock, used to form a given stent. That is, within a given catheter size, the internal diameter of the compressed (braided, knit or woven, or laser-cut) stent contained in the catheter will vary based on the sizes (diameters) of the wires, or the wall thickness of the tube stock, and possibly other parameters of the stent corresponding to different deployed sizes or target vessel sizes. This can require using different pad diameters to accommodate different stent sizes within a desired range (e.g. about 3.5 to 5 millimeters in pad diameter), which necessitates manufacturing the pads of various diameters to very small size tolerances. Embodiments of the present technology can allow a single size stent engagement member to be used with a relatively broad range of stent inner diameters within a given catheter size (e.g. a 0.027", 0.021", or 0.017" inner diameter catheter). For example, a stent engagement member comprising a rigid plate, sprocket or member that has a plurality of projections separated by recesses can be used to secure a range of different stent sizes within a given catheter.

Specific details of several embodiments of the present technology are described herein with reference to FIGS. 1-11C. Although many of the embodiments are described with respect to devices, systems, and methods for delivery of stents, tubular implants such as filters, shunts or stent-grafts and other medical devices, other applications and other embodiments in addition to those described herein are within the scope of the present technology, and can be employed in any of the embodiments of systems disclosed herein, in place of a stent as is typically disclosed. It should be noted that other embodiments in addition to those disclosed herein are within the scope of the present technology. Further, embodiments of the present technology can have different configurations, components, and/or procedures than those shown or described herein. Moreover, embodiments of the present technology can have configurations, components, and/or procedures in addition to those shown or described herein and that these and other embodiments may not have several of the configurations, components, and/or procedures shown or described herein without deviating from the present technology.

As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device. The headings provided herein are for convenience only and should not be construed as limiting the subject matter disclosed.

Selected Examples of Coupling Assemblies for Medical Device Delivery Systems

FIGS. 1-11C depict embodiments of medical device delivery systems that may be used to deliver and/or deploy a medical device, such as but not limited to a stent, into a hollow anatomical structure such as a blood vessel. The stent can comprise a braided stent or other form of stent such as a woven stent, knit stent, laser-cut stent, roll-up stent, etc. The stent can optionally be configured to act as a "flow diverter" device for treatment of aneurysms, such as those found in blood vessels including arteries in the brain or within the cranium, or in other locations in the body such as peripheral arteries. The stent can optionally be similar to any of the versions or sizes of the PIPELINE™ Embolization Device marketed by Medtronic Neurovascular of Irvine, Calif. USA. The stent can alternatively comprise any suitable tubular medical device and/or other features, as described herein. In some embodiments, the stent can be any one of the stents described in U.S. application Ser. No. 15/892,268, filed Feb. 8, 2018, titled VASCULAR EXPANDABLE DEVICES, the entirety of which is hereby incorporated by reference herein and made a part of this specification.

FIG. 1 is a schematic illustration of a medical device delivery system 100 configured in accordance with an embodiment of the present technology. The system 100 can comprise an elongate tube or catheter 101 which slidably receives a core member or core assembly 103 configured to carry a stent 105 through the catheter 101. The depicted catheter 101 has a proximal region 107 and an opposing distal region 109 which can be positioned at a treatment site within a patient, an internal lumen 111 extending from the proximal region 107 to the distal region 109, and an inner surface 113 defining the lumen 111. At the distal region 109, the catheter 101 has a distal opening 115 through which the core member 103 may be advanced beyond the distal region 109 to expand or deploy the stent 105 within the blood vessel 116. The proximal region 107 may include a catheter hub (not shown). The catheter 101 can define a generally longitudinal dimension extending between the proximal region 107 and the distal region 109. When the delivery system 100 is in use, the longitudinal dimension need not be straight along some or any of its length.

The core member 103 is configured to extend generally longitudinally through the lumen 111 of the catheter 101. The core member 103 can generally comprise any member(s) with sufficient flexibility and column strength to move the stent 105 or other medical device through the catheter 101. The core member 103 can therefore comprise a wire, tube (e.g., hypotube), braid, coil, or other suitable member(s), or a combination of wire(s), tube(s), braid(s), coil(s), etc.

The system 100 can also include a coupling assembly 120 or resheathing assembly 120 configured to releasably retain the medical device or stent 105 with respect to the core member 103. The coupling assembly 120 can be configured to engage the stent 105, via mechanical interlock with the pores and filaments of the stent 105, abutment of the proximal end or edge of the stent 105, frictional engagement with the inner wall of the stent 105, or any combination of these modes of action. The coupling assembly 120 can therefore cooperate with the overlying inner surface 113 of the catheter 101 to grip and/or abut the stent 105 such that the coupling assembly 120 can move the stent 105 along and within the catheter 101, e.g., distal and/or proximal movement of the core member 103 relative to the catheter 101 results in a corresponding distal and/or proximal movement of the stent 105 within the catheter lumen 111.

The coupling assembly 120 (or portion(s) thereof) can, in some embodiments, be configured to rotate about the core member 103. In some such embodiments, the coupling assembly 120 can comprise a proximal restraint 119 and a distal restraint 121. The proximal and distal restraints 119, 121 can be fixed to the core member 103 to prevent or limit proximal or distal movement of the coupling assembly 120 along the longitudinal dimension of the core member 103. For example, the proximal and distal restraints 119, 121 can be soldered or fixed with adhesive to the core wire 103. One or both of the proximal and distal restraints 119, 121 can have an outside diameter or other radially outermost dimension that is smaller than the outside diameter or other radially outermost dimension of the overall coupling assembly 120 such that one or both of the restraints 119, 121 do not contact the inner surface of the stent 105 during operation of the system 100. (In some embodiments, as described in further detail below, the proximal restraint 119 can be sized to abut the proximal end of the stent 105, and be employed to push the stent distally during delivery.) The distal restraint 121 can taper in the distal direction down towards the core member 103. This tapering can reduce the risk of the distal restraint 121 contacting an inner surface of the stent 105, particularly during navigation of tortuous vasculature, in which the system 100 can assume a highly curved configuration.

The coupling assembly 120 can also include first and second stent engagement members (or device engagement members, or resheathing members) 123*a-b* (together "engagement members 123") and first and second spacers 125*a-b* (together "spacers 125") disposed about the core member 103 between the proximal and distal restraints 119, 121. In the illustrated embodiment, from proximal to distal, the elements of the coupling assembly 120 include the proximal restraint 119, followed by the first spacer 125*a*, the first stent engagement member 123*a*, the second spacer 125*b*, the second stent engagement member 123*b*, and finally the distal restraint 121. In this configuration, the first spacer 125*a* defines the relative positioning of the first engagement member 123*a* and the proximal restraint 119. The second spacer 125*b* defines the relative longitudinal spacing between the first engagement member 123*a* and the second engagement member 123*b*.

As described in more detail below, one or both of the spacers 125 can take the form of a wire coil, a solid tube, or other structural element that can be mounted over the core member 103 to longitudinally separate adjacent components of the coupling assembly 120. In some embodiments, one or both of the spacers 125 can be a zero-pitch coil with flattened ends as described in more detail below with respect to FIGS. 4A and 4B. In some embodiments, one or both of the spacers 125 can be a solid tube (e.g., a laser-cut tube) that can be rotatably mounted or non-rotatably fixed (e.g., soldered) to the core member 103. The spacers 125 can have a radially outermost dimension that is smaller than a radially outermost dimension of the engagement members 123 such that the spacers 125 do not contact the stent 105 during normal operation of the system 100. As described in more detail below, the dimensions, construction, and configuration of the spacers 125 can be selected to achieve improved grip between the coupling assembly 120 and the overlying stent 105.

As described in more detail below with respect to FIGS. 3A, 3B, and 5A-11C, one or both of the stent engagement members 123 can be a rigid plate, sprocket or member with a central aperture configured to receive the core member 103 therethrough. The stent engagement members 123 are configured to mechanically interlock with or engage the stent 105 such that the stent engagement members 123 restrain the stent 105 from moving longitudinally with respect to the core member 103.

Although the embodiment illustrated in FIG. 1 includes two stent engagement members 123 and two spacers 125, the number of stent engagement members and spacers can vary. In at least one embodiment, the coupling assembly 120 includes only a single stent engagement member without any spacers. In other embodiments, the number of stent engagement members can vary, for example two, three, four, five, six, or more stent engagement members separated by spacers.

In the embodiment of the coupling assembly 120 depicted in FIG. 1, the proximal restraint 119 is configured to abut the proximal end or proximal edge of the stent 105. In this arrangement the proximal restraint 119 can be used to move (e.g., push) the stent 105 distally through the catheter 101 in response to a distal push force applied to the core member 103. Such a proximal restraint 119 can have a diameter that is slightly smaller than the inner diameter of the catheter 101, leaving a small circumferential or radial gap between the outer edge of the proximal restraint 119 and the inner wall of the catheter 101. In addition, the length of the proximal spacer 125*a* can be sized so that the proximal edge of the stent 105 abuts the distal face of the proximal spacer 119.

When the proximal restraint 119 is configured to push the stent 105 distally, the proximal restraint accordingly transmits some, most or all of the distal longitudinal (push) force to the stent 105, wholly or partially in place of the stent engagement member(s) 123. In such a configuration, the stent engagement members 123 can transmit little or no push force to the stent 105 while the stent 105 is delivered distally along the length of the catheter. Advantageously, this reduces or eliminates the tendency of the stent engagement member(s) 123 to distort the pores of the stent 105 with which the engagement members are engaged, when the engagement members are employed to transmit force to and move the stent 105 within the catheter 101. Use of the proximal restraint 119 to move the stent 105 in this manner can also reduce or eliminate longitudinal movement of the stent 105 relative to the core member 103 that sometimes accompanies the pore distortion described above. In most cases, the vast majority of the travel of the stent 105 within the catheter 101 is in the distal or "push" direction during delivery to the treatment location, in contrast to the relatively short travel involved in resheathing the stent 105, in the proximal or "pull" direction. Therefore, configuring the proximal restraint 119 to transmit most or all of the push force to the stent 105 can significantly reduce or substantially eliminate such distortion and/or relative longitudinal movement of the stent.

The coupling assembly 120 of FIG. 1 can therefore employ the proximal restraint 119 as a pushing element to transmit at least some, or most or all, distally-directed push force to the stent 105 during delivery. In such a coupling assembly 120, the stent engagement member(s) 123 do not transmit any distally-directed push force to the stent 105 during delivery (or transmit only a small portion of such force, or do so only intermittently). The stent engagement member(s) 123 can transmit proximally-directed pull force to the stent 105 during retraction or resheathing, and the proximal restraint 119 can transmit no proximally-directed pull force to the stent (or it may do so occasionally or intermittently, for example when a portion of the stent 105 becomes trapped between the outer edge of the proximal restraint 119 and the inner wall of the catheter 101).

In some embodiments of the coupling assembly 120 of FIG. 1, the first spacer 125*a* can be a rigid tube. Such a rigid tube can comprise a solid (e.g., lacking flexibility-enhancing cuts such as spiral cuts or periodic arcuate cuts) tube of rigid material, e.g. a metal or rigid polymer. The use of a rigid tube as the first spacer 125*a* tends to reduce or eliminate lateral bending of the delivery system 100 around the junction of the proximal restraint 119 and the first spacer 125*a* as the delivery system is advanced through a tortuous path. A lack of bending in this area can be advantageous when the proximal restraint 119 is employed as a pushing element, to transmit distally-directed push forces to the stent 105 during delivery. When bending occurs, the distal face of the proximal restraint 119 may become poorly engaged with the proximal end of the stent 105, for example engaged only along part of the circumference of the stent. This can lead to concentration of push force on only a small part of the stent, and/or slippage of the stent into the radial gap between the outer edge of the proximal restraint and the inner wall of the catheter 101. Any of these failure modes can adversely affect the function of the delivery system, damage the stent, or both.

In some embodiments, the stent engagement member(s) 123 are employed for both distal and proximal movement of the stent 105 with respect to the catheter 101. The engagement member(s) 123 transmit distally-directed force to the stent 105 to move it distally within the catheter 101 during delivery, and proximally-directed force to the stent 105 to move it proximally into the catheter 101 during resheathing. In such embodiments, the proximal restraint 119 can be made with a relatively small outer diameter, and/or be positioned sufficiently proximal of the proximal end of the stent 105, to prevent the proximal restraint 119 from transmitting distally-directed push forces to the stent 105 during delivery.

In operation, the stent 105 can be moved distally or proximally within the catheter 101 via the core member 103 and the coupling assembly 120. To move the stent 105 out of the catheter 101, either the core member 103 is moved distally while the catheter 101 is held stationary or the core member 103 is held stationary while the catheter 101 is withdrawn proximally. When the core member 103 is moved distally, the distal face of the proximal restraint 119 bears against the proximal end or edge of the stent 105 and causes the stent to be advanced distally, and ultimately out of the distal region 109 of the catheter 101. (In embodiments wherein the stent engagement member(s) 123 are employed to transmit pushing force to the stent 105, the mechanical engagement or interlock between the stent engagement members 123 and the stent 105, in response to the application of a distally-directed force to the core member 103, causes the stent 105 to move distally through and out of the catheter 101.) Conversely, to resheath or otherwise move the stent 105 into the catheter 101, the relative movement between the core member 103 and the catheter 101 is reversed compared to moving the stent 105 out of the catheter such that the proximal region of the distal restraint 121 bears against the distal region of the second spacer 125*b* and thereby causes the spacers 125 and the stent engagement members 123 to be retracted relative to the catheter 101. The mechanical engagement between the stent engagement members 123 and the stent 105 accordingly holds the stent 105 with respect to the core member 103 such that proximal movement of the stent 105 relative to the catheter 101 enables re-sheathing of the stent 105 back into the distal region 109 of the catheter 101. This is useful when the stent 105 has been partially deployed and a portion of the stent 105 remains disposed between at least one of the stent engagement members 123 (e.g. the first stent engagement member 123*a*) and the inner surface 113 of the catheter 101 because the stent 105 can be withdrawn back into the distal opening 115 of the catheter 101 by moving the core member 103 proximally relative to the catheter 101 (and/or moving the catheter 101 distally relative to the core member 103). Resheathing in this manner remains possible until the stent engagement members 123 and/or catheter 101 have been moved to a point where the first stent engagement member 123*a* is beyond the distal opening 115 of the catheter 101 and the stent 105 is released from between the first stent engagement member 123*a* and the catheter 101.

The stent engagement members 123 and the spacers 125 (or any of the engagement members or spacers disclosed herein) can be fixed to the core member 103 so as to be immovable relative to the core member 103, in a longitudinal/sliding manner and/or in a radial/rotational manner. Alternatively, the spacers 125 and/or the stent engagement members 123 can be coupled to (e.g., mounted on) the core member 103 so that the spacers 125 and/or the stent engagement members 123 can rotate about the longitudinal axis of the core member 103, and/or move or slide longitudinally along the core member 103. In such embodiments, the spacers 125 and/or the stent engagement members 123 can each have an inner lumen or aperture that receives the core member 103 therein such that the spacers 125 and/or the stent engagement members 123 can slide and/or rotate relative to the core member 103. Additionally, in such embodiments, the proximal and distal restraints 119, 121 can be spaced apart along the core member 103 by a longitudinal distance that is slightly greater than the combined length of the spacers 125 and the stent engagement members 123, so as to leave one or more longitudinal gaps between the first and second spacers 125*a-b*, respectively, and the proximal and distal restraints 119, 121. When present, the longitudinal gap(s) allow the spacers 125 and the stent engagement members 123 to slide longitudinally along the core member 103 between the restraints 119, 121. The longitudinal range of motion of the spacers 125 and the stent engagement members 123 between the restraints 119, 121 is approximately equal to the total combined length of the longitudinal gap(s), if any.

Instead of or in addition to the longitudinal gap(s), the coupling assembly 120 can include radial gaps between the outer surface of the core member 103 and the inner surface of the spacers 125 and the stent engagement members 123. Such radial gaps can be formed when the spacers 125 and/or the stent engagement members 123 are constructed with holes that are somewhat larger than the outer diameter of the corresponding portion of the core member 103. When present, the radial gaps allow the spacers 125 and/or the stent engagement members 123 to rotate about the longitudinal axis of the core member 103 between the restraints 119, 121. The presence of longitudinal gaps of at least a minimal size on either side of the spacers 125 and the stent engagement members 123 can also facilitate the rotatability of the spacers 125 and the stent engagement members 123.

In some embodiments, the stent engagement members 123 can be mounted onto the core member 103 to permit not only rotational movement but also a degree of tilting of the engagement members 123 with respect to a longitudinal axis of the core member 103. For example, the holes in the stent engagement members 123 can be larger than the outer diameter of the corresponding portion of the core member 103, thereby permitting both rotational movement and tilting with respect to the core member 103. "Tilting" as used herein means that the long axis of the stent engagement member 123 (i.e., an axis extending along the longest dimension of the stent engagement member 123, substantially parallel to the proximal-facing and distal-facing end faces of the stent engagement member 123) is non-orthogonal to a longitudinal axis of the core member 103. For example, in one tilted configuration, the long axis of the first stent engagement member 123*a* can intersect the core member 103 at approximately 85 degrees, indicating 5 degrees of tilt. Depending on the dimensions of the stent engagement members 123 and the core member 103, the degree of tilting permitted can vary. In some embodiments, one or both of the stent engagement members 123 can tilt with respect to the core member 103 by 30 degrees or less, 20 degrees or less, 10 degrees or less, or 5 degrees or less. In some embodiments, one or both of the stent engagement members 123 can tilt with respect to the core member by at least 5 degrees, by at least 10 degrees, by at least 20 degrees, or more.

By permitting one or both of the stent engagement members 123 to tilt with respect to the core member 103, the coupling assembly 120 can better navigate tortuous anatomy in which the delivery system 100 assumes highly curved states. Additionally, tilting of the stent engagement members 123 can facilitate resheathability of the overlying stent 105 from a partially deployed state. For example, a stent 105 can be in a partially deployed state when a portion of the stent 105 has been moved distally beyond a distal end 113 of the catheter 101 such that the stent 105 has been released from the second stent engagement member 123*b* yet the stent 105 remains engaged with the first stent engagement member 123*a*. From this partially deployed state, the stent 105 can be resheathed or recaptured by distally advancing the catheter 101 with respect to the coupling assembly 120 (or, alternatively, by proximally retracting the core member 103 and coupling assembly 120 with respect to the catheter 101). During this movement, as the stent 105 moves proximally with respect to the catheter 101, the stent 105 begins to collapse along its length until it assumes an outer diameter corresponding to the inner diameter of the catheter 101 and engages the second stent engagement member 123*b*. With continued distal movement of the catheter with respect to the coupling assembly 120, the second stent engagement member 123*b* is eventually received within the lumen 111 of the catheter 101, with the stent 105 interlocked with the stent engagement member 123*b* and held in that relationship by the catheter. When the second stent engagement member 123*b* initially contacts the distal end 113 of the catheter 101, there is some risk that the proximal-facing end face of the second stent engagement member 123*b* will abut the distal end 113 of the catheter 101, thereby inhibiting the second stent engagement member 123*b* from being retracted into the lumen 111 of the catheter 101. By allowing the second stent engagement member 123*b* to tilt with respect to the core member 103, when the proximal-facing end face of the second stent engagement member 123*b* abuts a distal end of the catheter 101, the second stent engagement member 123*b* can tilt to permit at least a portion of the second stent engagement member 223*b* to easily enter the lumen 111 of the catheter 101. Once at least a portion of the second stent engagement member 123*b* is positioned within the lumen 111, the coupling assembly 120 can continue to be retracted until the second stent engagement member 123*b* is fully received within the lumen 111, and the stent 105 can be fully resheathed or recaptured.

Figure 2:
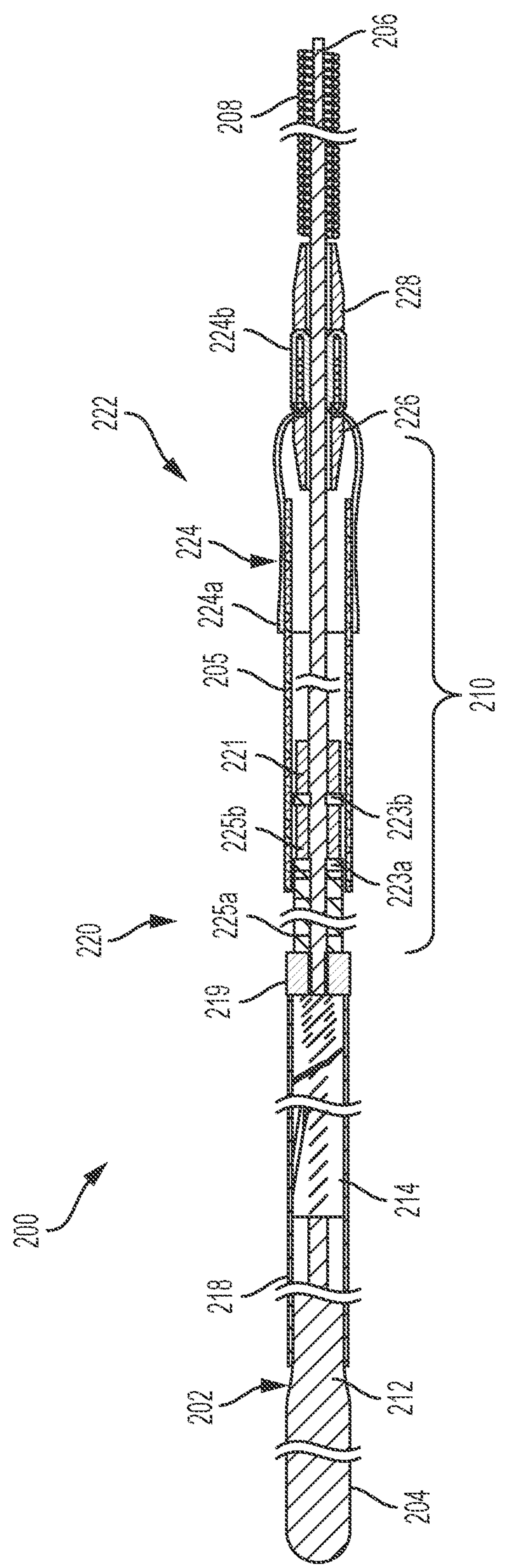
FIG. 2 is a side, cross-sectional view of a medical device delivery system, according to some embodiments.

FIG. 2 illustrates a side cross-sectional view of another embodiment of a medical device delivery system 200 configured in accordance with an embodiment of the present technology. The delivery system 200 can be configured to carry a stent (or other vascular implant or device) 205 thereon to be advanced through a surrounding catheter to a target site in a patient, similar to the operation described above with respect to FIG. 1. (The surrounding catheter is omitted in FIG. 2 for clarity). The delivery system 200 can be advanced distally with respect to a distal end of the catheter to expand or deploy the stent 205 at the target site.

The delivery system 200 can be used with any number of catheters. For example, the catheter can optionally comprise any of the various lengths of the MARKSMAN™ catheter available from Medtronic Neurovascular of Irvine, Calif. USA. The catheter can optionally comprise a microcatheter having an inner diameter of about 0.030 inches or less, and/or an outer diameter of 3 French or less near the distal region. Instead of or in addition to these specifications, the catheter can comprise a microcatheter which is configured to percutaneously access the internal carotid artery, or another location within the neurovasculature distal of the internal carotid artery.

The delivery system 200 can comprise a core member or core assembly 202 configured to extend generally longitudinally through the lumen of a catheter. The core member 202 can have a proximal region 204 and a distal region 206, which can optionally include a tip coil 208. The core member 202 can also comprise an intermediate portion 210 located between the proximal region 204 and the distal region 206. The intermediate portion 210 is the portion of the core member 202 onto or over which the stent 205 extends when the core member 202 is in the pre-deployment configuration as shown in FIG. 2.

The core member 202 can generally comprise any member(s) with sufficient flexibility and column strength to move a stent or other medical device through a surrounding catheter. The core member 202 can therefore comprise a wire, tube (e.g., hypotube), braid, coil, or other suitable member(s), or a combination of wire(s), tube(s), braid(s), coil(s), etc. The embodiment of the core member 202 depicted in FIG. 2 is of multi-member construction, comprising a wire 212 with a tube 214 surrounding the wire 212 along at least a portion of its length. An outer layer 218, which can comprise a layer of lubricious material such as PTFE (polytetrafluoroethylene or TEFLON™) or other lubricious polymers, can cover some or all of the tube 214 and/or wire 212. The wire 212 may taper or vary in diameter along some or all of its length. The wire 212 may include one or more fluorosafe markers (not shown), and such marker(s) can be located on a portion of the wire 212 that is not covered by the outer layer 218 (e.g., proximal of the outer layer 218). This portion of the wire 212 marked by the marker(s), and/or proximal of any outer layer 218, can comprise a bare metal outer surface.

The core member 202 can further comprise a proximal coupling assembly 220 and/or a distal interface assembly 222 that can interconnect the stent 205 with the core member 202. The proximal coupling assembly 220 can comprise one or more stent engagement members **223*a-b* (together "engagement members 223") that are configured to mechanically engage or interlock with the stent 205. In this manner, the proximal coupling assembly 220 cooperates with an overlying inner surface of a surrounding catheter (not shown) to grip the stent 205 such that the proximal coupling assembly 220 can move the stent 205 along and within the catheter, e.g., as the user pushes the core member 202 distally and/or pulls the core member proximally relative to the catheter, resulting in a corresponding distal and/or proximal movement of the stent 205** within the catheter lumen.

The proximal coupling assembly 220 can, in some embodiments, be similar to any of the versions or embodiments of the coupling assembly 120 described above with respect to FIG. 1. For example, the proximal coupling assembly 220 can include proximal and distal restraints 219, 221 that are fixed to the core member 202 (e.g., to the wire 212 thereof in the depicted embodiment) so as to be immovable relative to the core member 202, either in a longitudinal/sliding manner or a radial/rotational manner. The proximal coupling assembly 220 can also include a plurality of stent engagement members 223 separated by spacers **225*a-b* (together "spacers 225"). The stent engagement members 223 and spacers 225 can be coupled to (e.g., mounted on) the core member 202 so that the proximal coupling assembly 220 can rotate about the longitudinal axis of the core member 202 (e.g., of the intermediate portion 210), and/or move or slide longitudinally along the core member 202. In some embodiments, the proximal restraint 219 comprises a substantially cylindrical body with an outer diameter that is greater than or equal to an outer diameter of the first spacer 225*a*. The distal restraint 221 can taper in the distal direction down towards the core member 202. This tapering can reduce the risk of the distal restraint 221 contacting an inner surface of the overlying stent 205, particularly during navigation of tortuous vasculature, in which the system 200 can assume a highly curved configuration. In some embodiments, the distal restraint 221 can have an outside diameter or other radially outermost dimension that is smaller than the outside diameter or other radially outermost dimension of the overall proximal coupling assembly 220, so that distal restraint 221 will tend not to contact the inner surface of the overlying stent 205**.

In the proximal coupling assembly 220 shown in FIG. 2, the stent 205 can be moved distally or proximally within an overlying catheter (not shown) via the proximal coupling assembly 220. In some embodiments, the stent 205 can be resheathed via the proximal coupling assembly 220 after partial deployment of the stent 205 from a distal opening of the catheter, in a manner similar to that described above with respect to the coupling assembly 120 in FIG. 1.

The proximal coupling assembly 220 can be configured and function in a manner similar to the embodiment of the coupling assembly 120 depicted in FIG. 1. Specifically, the proximal restraint 219 can be made to function as a pushing element by appropriately sizing the outer diameter of the proximal restraint 219 and the length of the first spacer **225*a*, such that the distal face of the proximal restraint 219 abuts the proximal end or edge of the stent 105. When the proximal coupling element 220 is so arranged, the proximal restraint 219 can transmit at least some, or most or all, distally-directed push force to the stent 205 during delivery, and the stent engagement member(s) 223 do not transmit any distally-directed push force to the stent 205 during delivery (or transmit only a small portion of such force, or do so only intermittently). The stent engagement member(s) 223 can transmit proximally-directed pull force to the stent 205 during retraction or resheathing, and the proximal restraint 219 can transmit no proximally-directed pull force to the stent (or it may do so occasionally or intermittently, for example when a portion of the stent 205 becomes trapped between the outer edge of the proximal restraint 219 and the inner wall of the catheter). Again similarly to the coupling assembly 120 shown in FIG. 1, the first spacer 225*a* can optionally take the form of a solid tube when the proximal coupling assembly 220 includes a proximal restraint 219** configured as a pushing element.

Figure 3A:
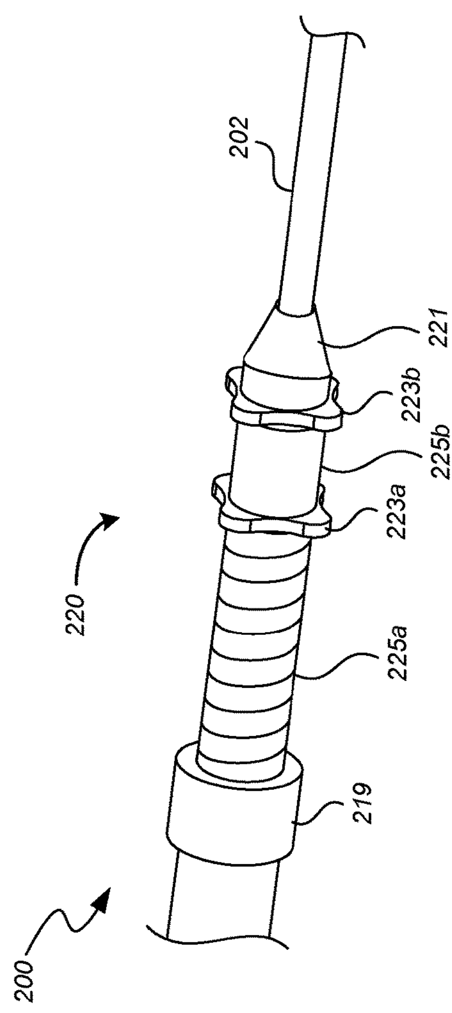
FIG. 3A is an enlarged perspective view of a coupling assembly having stent engagement members in accordance with some embodiments.
Figure 3B:
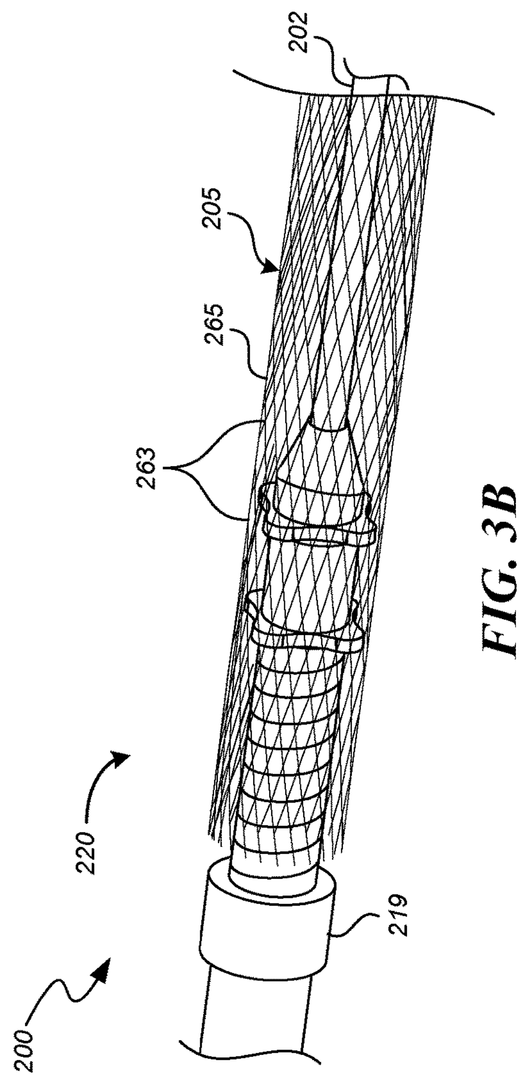
FIG. 3B is an enlarged perspective view of the coupling assembly of FIG. 3A with an overlying stent.

Although the proximal coupling assembly 220 can be configured in such a manner, with the proximal restraint 219 abutting the stent 205 so that the proximal restraint 219 can be used as a pushing element, the coupling assembly 220 is depicted with a different configuration in FIGS. 2 and 3A-3B. The depicted configuration entails use of the stent engagement members 223 for both distal (delivery) and proximal (resheathing) movement of the stent 205, as described elsewhere herein.

Optionally, the proximal edge of the proximal coupling assembly 220 can be positioned just distal of the proximal edge of the stent 205 when in the delivery configuration. In some such embodiments, this enables the stent 205 to be re-sheathed when as little as a few millimeters of the stent remains in the catheter. Therefore, with stents of typical length, resheathability of 75% or more can be provided (i.e. the stent can be re-sheathed when 75% or more of it has been deployed).

With continued reference to FIG. 2, the distal interface assembly 222 can comprise a distal engagement member 224 that can take the form of, for example, a distal device cover or distal stent cover (generically, a "distal cover"). The distal cover 224 can be configured to reduce friction between the stent 205 (e.g., a distal portion thereof) and the inner surface of a surrounding catheter. For example, the distal cover 224 can be configured as a lubricious, flexible structure having a free first end or section 224*a* that can extend over at least a portion of the stent 205 and/or intermediate portion 210 of the core member 202, and a fixed second end or section 224*b* that can be coupled (directly or indirectly) to the core member 202.

The distal cover 224 can have a first or delivery position, configuration, or orientation in which the distal cover can extend proximally relative to the distal tip, or proximally from the second section 224*b* or its (direct or indirect) attachment to the core member 202, and at least partially surround or cover a distal portion of the stent 205. The distal cover 224 can be movable from the first or delivery orientation to a second or resheathing position, configuration, or orientation (not shown) in which the distal cover can be everted such that the first end 224*a* of the distal cover is positioned distally relative to the second end 224*b* of the distal cover 224 to enable the resheathing of the core member 202, either with the stent 205 carried thereby, or without the stent 205. As shown in FIG. 2, the first section 224*a* of the distal cover 224 can originate from the proximal end of the second section 224*b*. In another embodiment, the first section 224*a* can originate from the distal end of the second section 224*b*.

The distal cover 224 can be manufactured using a lubricious and/or hydrophilic material such as PTFE or Teflon®, but may be made from other suitable lubricious materials or lubricious polymers. The distal cover can also comprise a radiopaque material which can be blended into the main material (e.g., PTFE) to impart radiopacity. The distal cover 224 can have a thickness of between about 0.0005" and about 0.003". In some embodiments, the distal cover can be one or more strips of PTFE having a thickness of about 0.001".

The distal cover 224 (e.g., the second end 224*b* thereof) can be fixed to the core member 202 (e.g., to the wire 212 or distal tip thereof) so as to be immovable relative to the core member 202, either in a longitudinal/sliding manner or a radial/rotational manner. Alternatively, as depicted in FIG. 2, the distal cover 224 (e.g., the second end 224*b* thereof) can be coupled to (e.g., mounted on) the core member 202 so that the distal cover 224 can rotate about a longitudinal axis of the core member 202 (e.g., of the wire 212), and/or move or slide longitudinally along the core member. In such embodiments, the second end 224*b* can have an inner lumen that receives the core member 202 therein such that the distal cover 224 can slide and/or rotate relative to the core member 202. Additionally, in such embodiments, the distal interface assembly 222 can further comprise a proximal restraint 226 that is fixed to the core member 202 and located proximal of the (second end 224*b* of the) distal cover 224, and/or a distal restraint 228 that is fixed to the core member 202 and located distal of the (second end 224*b* of the) distal cover 224. The distal interface assembly 222 can comprise a radial gap between the outer surface of the core member 202 (e.g., of the wire 212) and the inner surface of the second end 224*b*. Such a radial gap can be formed when the second end 224*b* is constructed with an inner luminal diameter that is somewhat larger than the outer diameter of the corresponding portion of the core member 202. When present, the radial gap allows the distal cover 224 and/or second end 224*b* to rotate about the longitudinal axis of the core member 202 between the restraints 226, 228.

In some embodiments, one or both of the proximal and distal restraints 226, 228 can have an outside diameter or other radially outermost dimension that is smaller than the (e.g., pre-deployment) outside diameter or other radially outermost dimension of the distal cover 224, so that one or both of the restraints 226, 228 will tend not to bear against or contact the inner surface of the catheter during operation of the core member 202. Alternatively, it can be preferable to make the outer diameters of the restraints 226 and 228 larger than the largest radial dimension of the pre-deployment distal cover 224, and/or make the outer diameter of the proximal restraint 226 larger than the outer diameter of the distal restraint 228. This configuration allows easy and smooth retrieval of the distal cover 224 and the restraints 226, 228 back into the catheter post stent deployment.

In operation, the distal cover 224, and in particular the first section 224*a*, can generally cover and protect a distal region of the stent 205 as the stent 205 is moved distally through a surrounding catheter. The distal cover 224 may serve as a bearing or buffer layer that, for example, inhibits filament ends of the distal region of the stent 205 (where the stent comprises a braided stent) from contacting an inner surface of the catheter, which could damage the stent 205 and/or catheter, or otherwise compromise the structural integrity of the stent 205. Since the distal cover 224 may be made of a lubricious material, the distal cover 224 may exhibit a low coefficient of friction that allows the distal region of the stent to slide axially within the catheter with relative ease. The coefficient of friction between the distal cover and the inner surface of the catheter can be between about 0.02 and about 0.4. For example, in embodiments in which the distal cover and the catheter are formed from PTFE, the coefficient of friction can be about 0.04. Such embodiments can advantageously improve the ability of the core member 202 to pass through the catheter, especially in tortuous vasculature.

Structures other than the herein-described embodiments of the distal cover 224 may be used in the core member 202 and/or distal interface assembly 222 to cover or otherwise interface with the distal region of the stent 205. For example, a protective coil or other sleeve having a longitudinally oriented, proximally open lumen may be employed. In other embodiments, the distal interface assembly 222 can omit the distal cover 224, or the distal cover can be replaced with a component similar to the proximal coupling assembly 220. Where the distal cover 224 is employed, it can be connected to the distal tip coil 208 (e.g., by being wrapped around and enclosing some or all of the winds of the coil 208) or being adhered to or coupled to the outer surface of the coil by an adhesive or a surrounding shrink tube. The distal cover 224 can be coupled (directly or indirectly) to other portions of the core member 202, such as the wire 212.

In embodiments of the core member 202 that employ both a rotatable proximal coupling assembly 220 and a rotatable distal cover 224, the stent 205 can be rotatable with respect to the core member 202 about the longitudinal axis thereof, by virtue of the rotatable connections of the proximal coupling assembly 220 and distal cover 224. In such embodiments, the stent 205, proximal coupling assembly 220 and distal cover 224 can rotate together in this manner about the core member 202. When the stent 205 can rotate about the core member 202, the core member 202 can be advanced more easily through tortuous vessels as the tendency of the vessels to twist the stent 205 and/or core member 202 is negated by the rotation of the stent 205, proximal coupling assembly 220, and distal cover 224 about the core member 202. In addition, the required push force or delivery force is reduced, as the user's input push force is not diverted into torsion of the stent 205 and/or core member 202. The tendency of a twisted stent 205 and/or core member 202 to untwist suddenly or "whip" upon exiting tortuosity or deployment of the stent 205, and the tendency of a twisted stent to resist expansion upon deployment, are also reduced or eliminated. Further, in some such embodiments of the core member 202, the user can "steer" the core member 202 via the tip coil 208, particularly if the coil 208 is bent at an angle in its unstressed configuration. Such a coil tip can be rotated about a longitudinal axis of the system 200 relative to the stent, coupling assembly 220 and/or distal cover 224 by rotating the distal region 206 of the core member 202. Thus the user can point the coil tip 208 in the desired direction of travel of the core member 202, and upon advancement of the core member the tip will guide the core member in the chosen direction.

FIG. 3A is an enlarged perspective view of the coupling assembly 220 of the medical device delivery system 200, and FIG. 3B illustrates the coupling assembly 220 with an overlying stent 205. The coupling assembly 220 includes first and second engagement members 223*a-b* mounted over the core member 202 adjacent to first and second spacers 225*a-b*. The proximal restraint 219 is disposed proximally to the proximal-most spacer 225*a*, and the distal restraint 221 is disposed distally to the distal-most engagement member 223*b*. As shown in FIG. 3B, the first and second stent engagement members 223*a* and 223*b* can interlock with the stent 205, e.g. by projecting into the pores thereof. The engagement members 223 can thereby secure the stent 205, in cooperation with an overlying catheter (not shown).

Figure 4A:
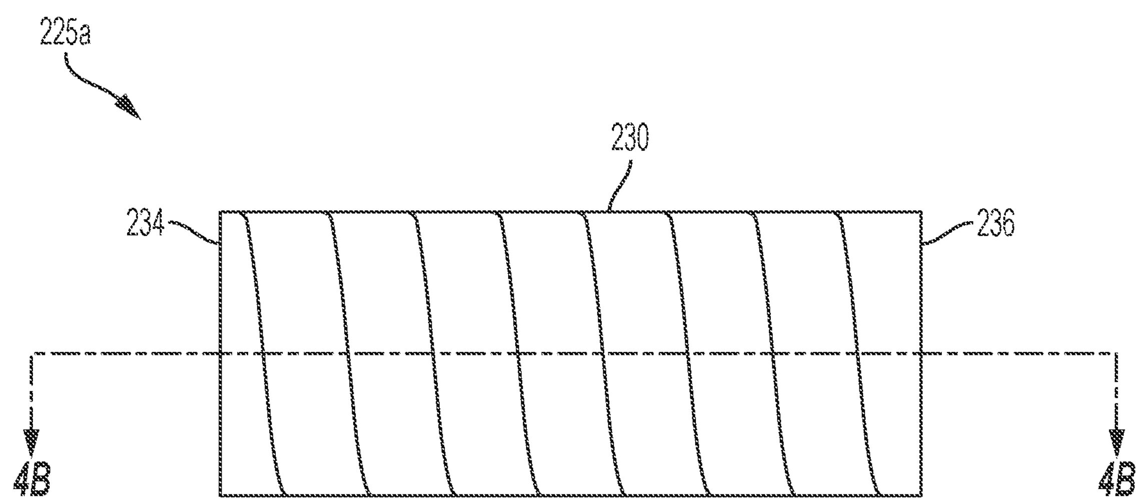
FIGS. 4A and 4B are side and side cross-sectional views, respectively, of a spacer of the coupling assembly shown in FIGS. 2-3B.
Figure 4B:
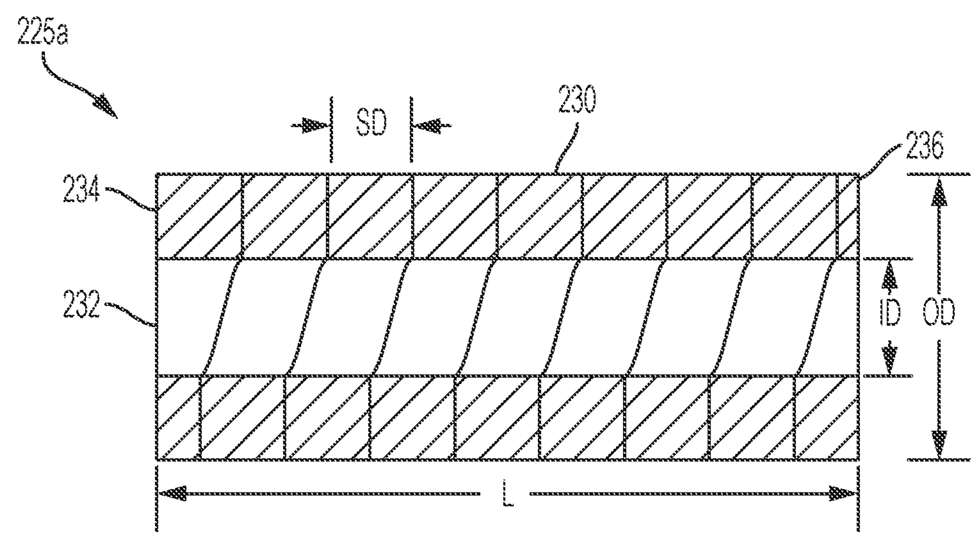

FIGS. 4A and 4B are side and cross-sectional views, respectively of a spacer configuration which can serve as the first spacer 225*a* of the coupling assembly 220, or as any spacer of any embodiment of the coupling assemblies or delivery systems disclosed herein. In at least some embodiments, the first spacer 225*a* includes a wire coil 230 defining a central lumen 232 through which the core member 202 extends. The coil 230 can have a proximal end face 234 and an opposing distal end face 236. The end faces 234, 236 can be substantially planar and substantially orthogonal to a longitudinal axis of the coil 230. For example, in some embodiments the end faces 234, 236 can be ground, polished, or otherwise flattened to provide planar surfaces that are substantially orthogonal to a long axis of the spacer 225*a*. This can improve the pushability or column strength of the overall system 200 as the planar surface increases the contact area between the proximal restraint 219 and the proximal end face 234, and also increase the contact area between the distal end face 236 of the spacer 225*a* and the first stent engagement member 223*a*.

In some embodiments, the coil wire 230 is a zero-pitch coil configured such that, in an unconstrained condition, each winding of the coil 230 is in direct contact with an adjacent winding of the coil 230. In such embodiments, the coil 230 can be substantially incompressible along an axial direction under the forces typically encountered during use of the delivery system 200. This incompressibility can provide the pushability of a solid tube spacer while also permitting the bending flexibility of a coil. During bending of the coil 230, one or more of the windings of the coil 230 may become partially separated from one another to accommodate the bending movement. In the absence of external forces, the coil 230 can return to its unconstrained state (i.e., having zero pitch).

With continued reference to FIGS. 4A and 4B, the lumen 232 of the coil 230 can define an inner diameter ID that is slightly larger than a corresponding outer diameter of the core member 202. For example, in some embodiments the lumen 232 can have a diameter of approximately between about 0.008"-0.02", or between about 0.0160"-0.018", or between about 0.0165"-0.017". In at least some embodiments, the coil 230 can be free to rotate with respect to the core member 202. In other embodiments, the coil wire 230 can be rotationally fixed with respect to the core member 202, for example by attaching all or a portion of the coil 230 to the core member 202 using solder, adhesive, or other attachment technique. In some embodiments, the coil 230 can have a radially outermost diameter (OD) that is smaller than a radially outermost diameter of the stent engagement members 223 (FIGS. 3A and 3B) such that the coil 230 does not contact the overlying stent 205 during normal operation of the delivery system 200. In some embodiments, the radially outermost diameter OD of the coil 230 can be between about 0.008"-0.02", or between about 0.016"-0.018", or between about 0.0165"-0.017".

In some embodiments, the wire that forms the coil 230 can have an individual thickness or strand diameter SD (FIG. 4B) of between about 0.0015-0.006", or approximately 0.005". The wire forming the coil 230 can have a square or rectangular cross-section along its length. With such a square or rectangular cross-section, the wire can form winds having flat surfaces that face in the distal and proximal directions. Longitudinally adjacent flat surfaces contact each other and the flat nature of the surfaces provides for a stable, non-bending structure under longitudinally compressive loads. At the same time, the overall coil configuration of the spacer is flexible and bendable under bending loads. The longitudinal length L of the spacer 225 can vary according to the desired positioning between a proximal restraint 219 and the first stent engagement member 223*a* (FIGS. 3A and 3B). For example, in some embodiments the longitudinal length L can be between about 0.03"-0.05", or between about 0.036"-0.042", or approximately 0.039". In other embodiments, as mentioned above, the first spacer 225*a* can be a rigid and/or solid tube.

In some embodiments, the second spacer 225*b* can be configured similarly to the first spacer 225*a*, i.e., the second spacer 225*b* can also be a coil such as a zero-pitch coil rotatably mounted over the core member 202. In other embodiments, the second spacer 225*b* can be a solid tubular member. The second spacer 225*b* can have a substantially cylindrical outer surface, substantially planar proximal and distal end faces, and an inner lumen configured to slidably receive the core member 202 therethrough. As described in more detail below, the second spacer 225*b* can also be configured to have a longitudinal length to separate the first engagement member 223*a* and the second engagement member 223*b* by a desired amount. For example, in at least some embodiments, the second spacer 225*b* can have a length such that the first engagement member 223*a* is separated from the second engagement member 223*b* by approximately 1-3 times the pore pitch of the overlying stent 205, for example in some embodiments approximately equal to the pore length of the overlying stent 205.

In some embodiments, the first spacer 225*a* and/or the second spacer 225*b* can be coated with a lubricious material, for example PTFE, parylene, or other coating. The coating can be provided along an outer surface of the spacer 225, within an interior lumen (e.g., lumen 232 of the coil 230), or both. In some embodiments, the lubricious coating improves the rotatability of the spacer 225 with respect to the core member 202 and can also reduce friction between the spacer

225 and the overlying stent 205 or catheter in the event that the spacer 225 contacts these components during use of the delivery system 200.

Figure 5B:
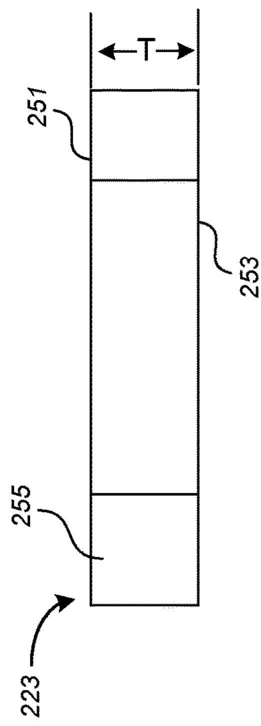
FIGS. 5A-5C are side, top, and perspective views, respectively, of an individual engagement member of the coupling assembly shown in FIGS. 2-3B.
Figure 5C:
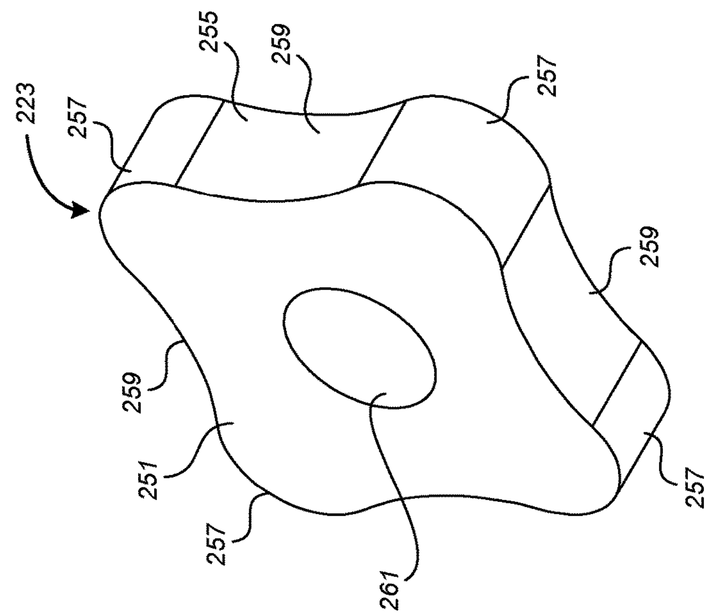
Figure 5A:
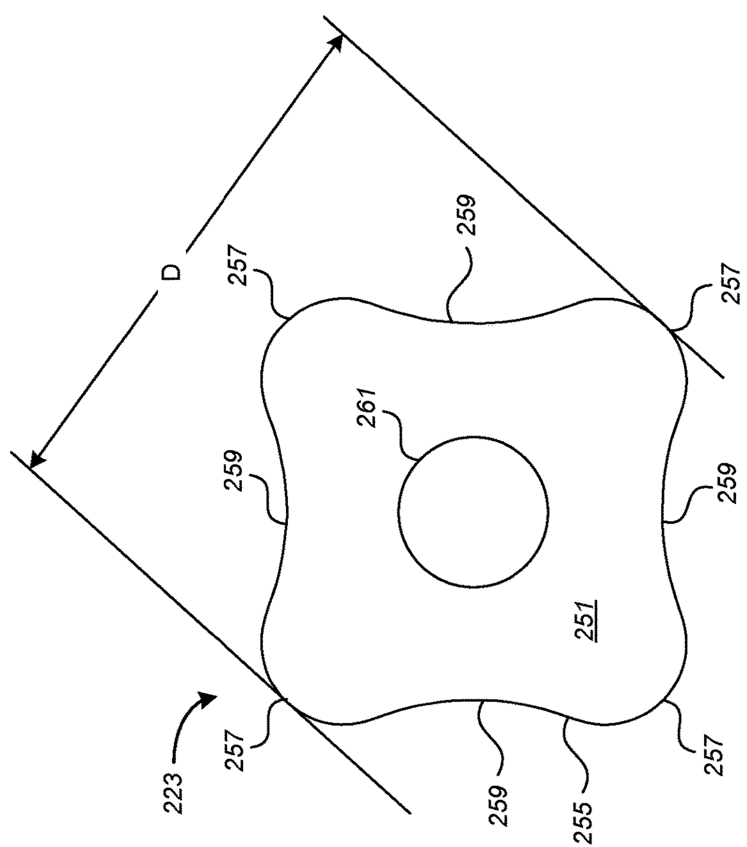
Figure 6A:
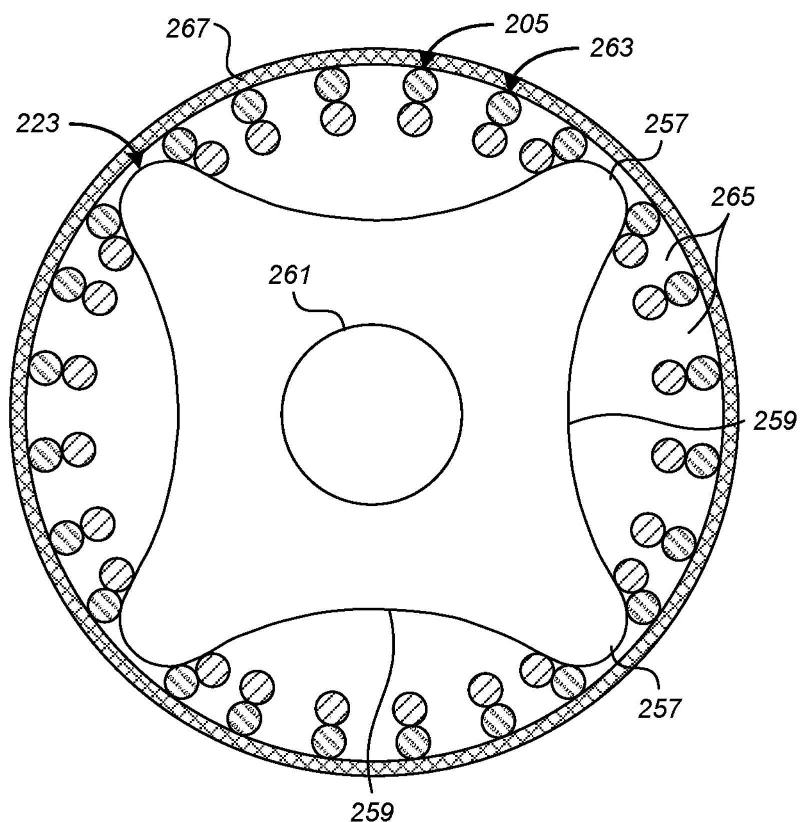
FIG. 6A is a schematic cross-sectional view of an engagement member and the stent of FIG. 3B.
Figure 6B:
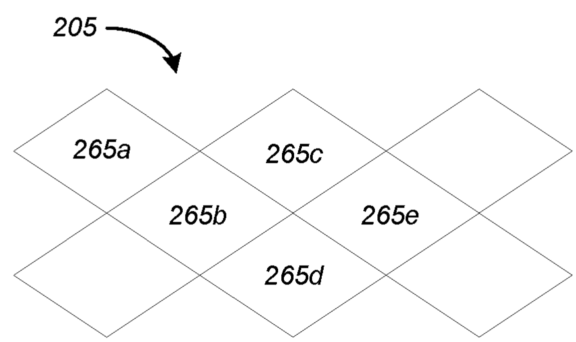
FIG. 6B is an enlarged detail view of a portion of the stent shown in FIG. 3B.

FIGS. 5A-5C are side, end, and perspective views, respectively, of a stent engagement member 223 of the coupling assembly 220 shown in FIGS. 3A and 3B. FIG. 6A is a schematic cross-sectional view of the stent engagement member 223 engaging the stent 205 within an overlying catheter 267, and FIG. 6B is an enlarged detail view of a portion of the stent 205. The depicted stent 205 is braided (although other types of stent, as disclosed elsewhere herein may be used) and includes a mesh 263 forming a plurality of pores 265 which are bounded by filaments, wires or struts and separated by points where the filaments, wires or struts cross (e.g., in the case of a braided or woven device) or intersect (e.g., in the case of a laser-cut device).

Referring to FIGS. 3A, 3B, and 5A-6B together, each of the stent engagement members 223 can have a plate-like or sprocket-like configuration with first and second end faces 251, 253 and a side surface 255 extending between the first and second end faces 251, 253. In the assembled delivery system 200, the first and second end faces 251, 253 can be oriented and maintained substantially orthogonal to a long axis of the core member 202 (or the engagement members can be configured to tilt to a desired degree, as discussed elsewhere herein). This can be achieved by configuring the spacers 225 with distal and proximal end faces that are orthogonal to the longitudinal axis of each spacer 225 (and/or to the core member 202), and/or minimizing the amount of longitudinal movement space (or "play") among the stent engagement members and spacers of the coupling assembly 220. Each stent engagement member forms a plurality of radially extending projections 257 separated by recesses 259. In the illustrated embodiment, there are four projections 257 separated by four recesses 259. However, in other embodiments the number of projections can vary, for example two, three, four, five, six, seven, or more projections separated by a corresponding number of recesses.

In some embodiments, the projections 257 include rounded edges or convex portions and the recesses 259 include rounded depressions or convex portions. During use of the delivery system 200, the rounded edges can reduce scraping of the projections 257 against the inner wall of an overlying catheter 267, which reduces generation of particulates and damage to the catheter 267. When the delivery system 200 is used with a braided stent such as the depicted stent 205, the recesses 259 can be sized to accommodate the thickness of braid wire crossings such that each projection 257 can extend at least partially into a pore 265 of the stent 205 between the adjacent wire crossings and the wire crossings surrounding the pore 265 can be at least partially received within the recesses 259 of the stent engagement member. In other embodiments, the projections and/or the recesses can assume other forms, for example with sharper or flatter peaks formed by the projections 257.

Each stent engagement member 223 can include an opening or central aperture 261 configured to receive the core member 202 therethrough. The opening of the aperture 261 can be larger than the diameter of the core member 202 such that the stent engagement members 223 can rotate about the long axis of the core member 202. As noted above, in some embodiments, the aperture 261 can be sufficiently larger than the diameter of the core member 202 to permit a degree of tilting of the engagement members 223 with respect to a longitudinal axis of the core member 202.

The stent engagement members 223 can be made to have a relatively thin and/or plate-like or sprocket-like configuration. Such a configuration can facilitate the formation of projections 257 that are small enough to fit inside the pores 265 of the stent 205. Accordingly, the stent engagement members 223 may be characterized by a largest radial dimension or diameter D along the first and second end faces 251, 253, and a thickness T measured along the side surface 255. In some embodiments, the diameter D is at least five times greater than the thickness T. In at least one embodiment, the thickness T is between approximately 25-200 microns, or 50-100 microns, for example, approximately 80 microns.

To effectively push or pull the stent 205 along a surrounding catheter, the stent engagement members 223 can be made to be rigid (e.g., incompressible by the forces encountered in typical use of the delivery system). The rigidity of the stent engagement members 223 can be due to their material composition, their shape/construction, or both. In some embodiments, the stent engagement members 223 are made of metal (e.g., stainless steel, Nitinol, etc.) or rigid polymers (e.g., polyimide, PEEK), or both. In some embodiments, even if the stent engagement member is made of a rigid material, based on structural characteristics the stent engagement member itself may be non-rigid and at least partially compressible.

As noted above, the spacers 225 can be substantially cylindrical bodies having a smaller outer diameter than a largest outer diameter of the stent engagement members 223. In some embodiments, the spacers 225 include a central aperture sized and configured to allow the spacers 225 to be rotatably mounted over the core member 202. As mentioned previously, the spacers 225 can have end walls that are orthogonal to a long axis of the core member 202. These orthogonal end walls can help preserve the orthogonal orientation of the stent engagement members 223 relative to the core member 202 to prevent loss of engagement with stent 205. (Alternatively, the engagement members can be configured to tilt to a desired degree, as discussed elsewhere herein.) As described above, in some embodiments one or both of the first and second spacers 225*a* and 225*b* can be a wire coil defining a cylindrical body mounted over the core member 225*a*, for example a zero-pitch coil. In other embodiments, one or both of the first and second spacers 225*a* and 225*b* can take other forms, for example a solid cylindrical tube or other element coupled to the core member 202.

In some embodiments, the coupling assembly 220 can be configured to engage only a proximal portion (e.g., the proximalmost 5%, the proximalmost 10%, the proximalmost 20%, only a proximal half, etc.) of the stent 205. In other embodiments, coupling assembly 220 can engage the stent 205 along substantially its entire length.

The stent engagement members 223 can mechanically interlock with or engage the stent 205 such that each projection 257 is at least partially received within one of the pores 265. In some embodiments, the first engagement member 223*a* can engage with a proximal portion of the stent 205, for example at a position less than 5 pores or pore lengths away from a proximal end of the stent, or less than 3 pores or pore lengths away from the proximal end of the stent 205, etc. The spacers 225 can be configured with a length such that the projections 257 of adjacent stent engagement members 223 (e.g., the first stent engagement member 223*a* and adjacent second stent engagement member 223*b*) are spaced apart longitudinally by a distance that is substantially equal to the "pore length" (or "pore pitch") of the stent 205 (defined herein as the longitudinal distance between the centers of longitudinally adjacent and nonoverlapping pores 265 when the stent is in the compressed configuration wherein the outer diameter of the stent is equal to the inner diameter of the catheter) or, in some embodiments, a whole-number multiple of the pore length of the stent 205. For example, in some embodiments, the first and second stent engagement members 223*a* and 223*b* are spaced apart by between about 1-3 times the pore length of the stent 205 when the stent is at the inner diameter of the catheter 267. Accordingly, each projection can extend into and engage one of the pores 265 of the stent 205.

FIG. 6B is a schematic illustration of a portion of the stent 205, which includes a plurality of pores 265*a*-265*d*. As noted above, projections 257 of the stent engagement member 223 can engage individual pores 265 of the stent 205. In some embodiments, adjacent stent engagement members 223 engage longitudinally adjacent pores 265 of the stent 205. As used herein, "longitudinally adjacent" means that there is not an intervening pore in the longitudinal direction between the two pores. Longitudinally adjacent pores, however, can be non-adjacent radially, e.g., a first pore located at the "twelve o'clock" position on the circumference of the stent can be longitudinally adjacent to a second pore located at the "six o'clock" position on the circumference of the stent (or at any point on the circumference in between) if, in the longitudinal direction, there is no intervening pore between the two. For example, referring to FIG. 6B, the first pore 265*a* is longitudinally adjacent to each of the second pore 265*b*, the third pore 265*c*, and the fourth pore 265*d*. However, the first pore 265*a* is not longitudinally adjacent to the fifth pore 265*e*, because there are intervening pores between the two. In other embodiments, adjacent stent engagement members 223 engage pores which are not longitudinally adjacent but are spaced apart longitudinally by one or more intervening pores, for example the first pore 265*a* and the fifth pore 265*e*. Therefore, the first and second stent engagement members 223*a* and 223*b* can be spaced apart from one another by a longitudinal distance corresponding to the pore pitch of the stent 205, or by a longitudinal distance corresponding to a whole number multiple of the pore pitch.

In some embodiments, the longitudinal spacing between the first and second stent engagement members 223*a* and 223*b* can be slightly less than the pore length (e.g., 50% less, 40% less, 30% less, 20% less, 10% less, or 5% less than the pore length, etc.), or slightly less than a whole number multiple of the pore length (e.g., less by a decrement equal to 50%, 40%, 30%, 20%, 10%, or 5% of a single pore length, etc.). This slightly smaller spacing between the first and second stent engagement members 223*a* and 223*b* can provide improved grip on the stent 205 by minimizing the longitudinal "play" between the projections 257 of the first and second engagement members 223*a* and 223*b* and the wire crossing(s) or intersection point(s) positioned between the engagement members. As a result, a longitudinal movement of the core member causes a corresponding longitudinal movement of the stent with minimal delay and high precision. For example, a proximal movement of the core member (and/or the engagement member(s) carried thereby) causes a proximal movement of the stent, with the engagement member(s) moving no more than a first lag distance relative to the stent before initiating proximal movement of the stent. The first lag distance can be more than 40% of the pore length of the stent, or no more than 33%, or no more than 25%, or no more than 20%, or no more than 15%, or no more than 10%, or no more than 5% of the pore length. Instead of or in addition to such a first pore length, a distal movement of the core member (and/or the engagement member(s) carried thereby) causes a distal movement of the stent, with the engagement member(s) moving no more than a second lag distance relative to the stent before initiating distal movement of the stent. The second lag distance can be more than 40% of the pore length of the stent, or no more than 33%, or no more than 25%, or no more than 20%, or no more than 15%, or no more than 10%, or no more than 5% of the pore length.

The interaction between the projections 257 and the pores 265 can produce a mechanical interlock between stent engagement member 223 and the pores 265. This is in contrast to a conventional compressible pad that resiliently pushes against the stent as a whole, including the wire crossings. In at least some embodiments, the mechanical interlock provided by the stent engagement members 223 secures the stent 205 without pressing against the wire crossings of the stent 205. In some embodiments, the stent engagement members 223 are configured to secure a range of different stent sizes within a given catheter size (e.g., within a 0.017", 0.021" or 0.027" catheter (inside diameter)).

The stent engagement members 223 can be made of substantially rigid materials, for example metal, biocompatible polymers (e.g., PEEK), or other suitable materials. In some embodiments, the stent engagement members 223 can be made of stainless steel and manufactured using laser cutting followed by electropolishing. For example, a plurality of engagement members can be laser-cut from a sheet of stainless steel having the desired thickness (e.g., approximately 100 microns thick). Electropolishing can further reduce the thickness of the resulting stent engagement members, for example from 100 microns to approximately 80 microns. In other embodiments, the stent engagement members can be manufactured using other techniques, for example injection molding, chemical etching, or machining.

Note that various components of the delivery system 200 of FIGS. 2-6 can be incorporated into the delivery system 100 of FIG. 1, and vice versa. For example, any of the disclosed embodiments of the coupling assembly 220 can be employed as the coupling assembly 120 of the delivery system 100. Similarly, any of the embodiments of the stent engagement members 223 can be employed as the stent engagement member(s) 123 of the delivery system 100, and/or any of the embodiments of the spacers 225 can be employed as the spacer(s) 125 of the delivery system 100. Although many embodiments discussed herein include two engagement members 223, in other embodiments the delivery system 200 can include three, four, or more engagement members separated from one another by additional spacers. The spacing of such additional engagement members can be regular or irregular. For example, in one embodiment a third engagement member can be provided at a position configured to engage a distal region of the overlying stent, while the first and second engagement members engage only a proximal region of the overlying stent.

Additional Examples of Stent Engagement Members for Coupling Assemblies

In various embodiments, the stent engagement members of the coupling assembly can take additional forms. For example, the number of projections, the contours of the projections and recesses, the material selected, and dimensions can all vary to achieve desired operation of the coupling assembly. FIGS. 7A-11C illustrate various alternative embodiments of stent engagement members. These stent engagement members can be incorporated into and combined with the coupling assemblies 120 and 220 described above with respect to FIGS. 1-6. Additionally, aspects of these stent engagement members can be combined and intermixed such that features of any one of these stent engagement members (e.g., the number of protrusions or recesses, etc.) can be combined with the features of any of the other stent engagement members disclosed herein (e.g., the width of the contact region, spacing of the protrusions, etc.). In some embodiments, the individual stent engagement members of a given coupling assembly can be substantially identical in shape, size, and construction. In other embodiments, however, the properties of the individual stent engagement members can vary within a single coupling assembly, such as having different sizes, shapes, or material construction. For example, a single coupling assembly can have a first stent engagement member having a given number of protrusions, and a second stent engagement member having a different number of protrusions.

Figure 7A:
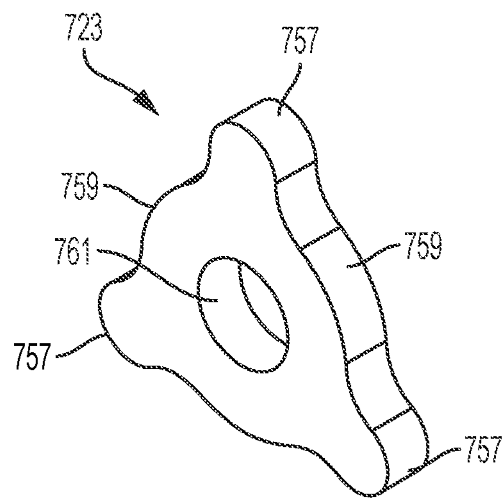
FIG. 7A is a perspective view of another embodiment of an engagement member.
Figure 7B:
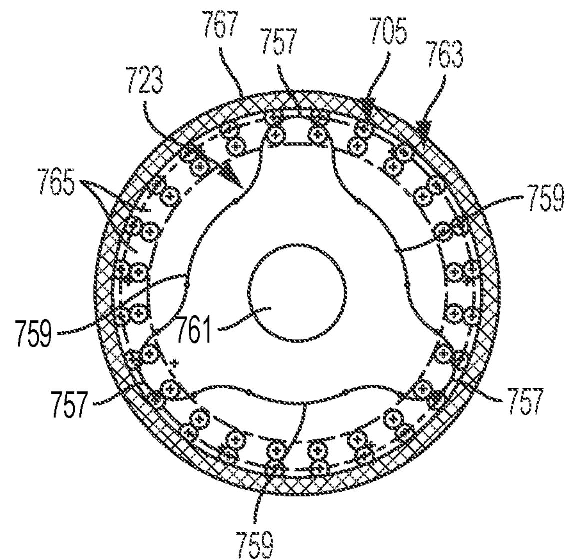
FIG. 7B is a schematic cross-sectional view of the engagement member of FIG. 7A engaged with an overlying stent.

FIG. 7A illustrates a perspective view of another embodiment of a stent engagement member 723, and FIG. 7B illustrates a cross-sectional view of the stent engagement member 723 of FIG. 7A engaged with an overlying stent 705 disposed within a catheter 767. Embodiments of the engagement member 723 can be similar to those described above with respect to the engagement member 223, except that the engagement member 723 includes three projections 757 separated by three recesses 759. The engagement member 723 engages and mechanically interlocks with an overlying stent 705, and the surrounding catheter 767 helps maintain such engagement until the interlocked portion of the stent exits the catheter. The stent 705 includes a mesh 763 defining a plurality of pores 765 which are separated by points where the wires, filaments, struts etc. of the mesh 763 cross (e.g., in the case of a braided stent) or intersect (e.g., in the case of a laser-cut stent). The radially extending projections 757 can each extend at least partially into a pore 765 of the stent 705 between adjacent crossing or intersection points and the crossing or intersection points surrounding the pore 765 can be at least partially received within the recesses 759 of the stent engagement member 723. In other embodiments, the projections and/or the recesses can assume other forms, for example with sharper or flatter peaks formed by the projections 759. The stent engagement member 723 includes an opening or central aperture 761 configured to receive a core member or core assembly therethrough. The opening of the aperture 761 can be larger than the diameter of the core member such that the stent engagement member 763 can rotate about the long axis of the core member. As noted above, in some embodiments, the aperture 761 can be sufficiently larger than the diameter of the core member to permit a degree of tilting of the engagement member 723 with respect to a longitudinal axis of the core member.

Figure 8A:
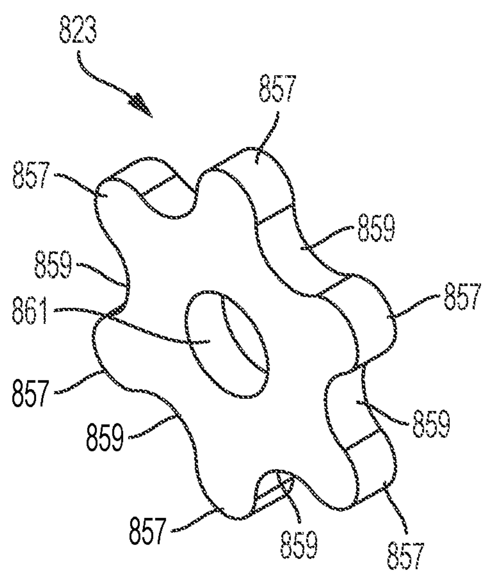
FIG. 8A is a perspective view of another embodiment of an engagement member.
Figure 8B:
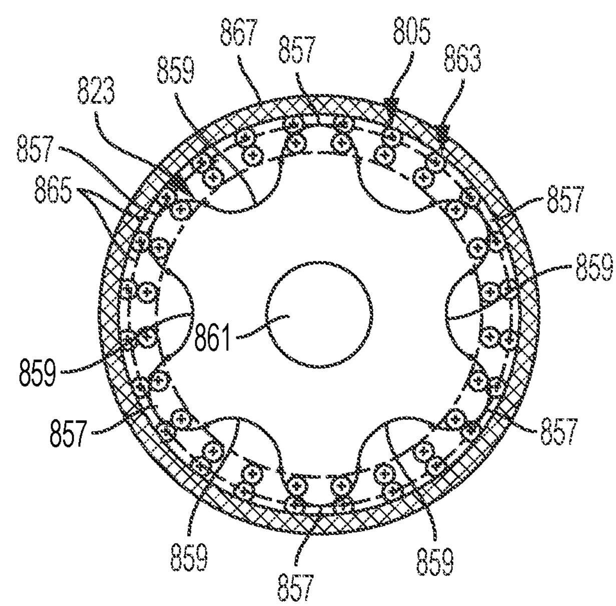
FIG. 8B is a schematic cross-sectional view of the engagement member of FIG. 8A engaged with an overlying stent.

FIG. 8A illustrates a perspective view of another embodiment of a stent engagement member 823, and FIG. 8B illustrates a cross-sectional view of the stent engagement member 823 of FIG. 8A engaged with an overlying stent 805 disposed within a catheter 867. Embodiments of the engagement member 823 can be similar to those described above with respect to the engagement members 223 and 723, except that the engagement member 823 includes six projections 857 separated by six recesses 859. The stent 805 includes a mesh 863 defining a plurality of pores 865 which are separated by points where the wires, filaments, struts, etc. of the mesh cross or intersect. The radially extending projections 857 can each extend at least partially into a pore 865 of the stent 805 between adjacent crossing or intersection points, and the crossing or intersection points surrounding the pore 865 can be at least partially received within the recesses 859 of the stent engagement member 823. In other embodiments, the projections and/or the recesses can assume other forms, for example with sharper or flatter peaks formed by the projections 859. A central aperture 861 can be configured to receive a core member or core assembly therethrough and can be sized to permit the stent engagement member 823 to rotate and/or tilt with respect to the core member.

Depending on the particular construction of the overlying stent 705, 805, in some embodiments the protrusions 757, 857 of the stent engagement members 723, 823 can be radially evenly spaced around the engagement members. For example, with respect to FIG. 7B, the center point of each protrusion 759 can be separated from the next protrusion 759 by 120 degrees. Similarly, as shown in FIG. 8B, the six protrusions 857 of the stent engagement member 823 can be radially evenly spaced around the engagement member 823, such that each protrusion 857 is separated from an adjacent protrusion 857 by 60 degrees. In braided stents, the number of strands defines the number of available pores radially aligned along any particular longitudinal location of the stent. For example, FIGS. 7B and 8B illustrate a cross-sectional views of 48-wire braided stents 705, 805 engaged with the stent engagement members 723 and 823, respectively. The 48-wire stents 705, 805 each defines 24 pores 765, 865 around the circumferences of the stents 705, 805. In some embodiments, aligning each protrusion 757, 857 with a pore 765, 865 improves the strength with which the stent engagement member 723, 823 interlocks with the overlying stent 705, 805, as well as overall mechanical fit and compatibility. Accordingly, it can be advantageous to align the protrusions 757, 857 with pores 765, 865 of the overlying stents 705, 805. Since the stent 705 of FIG. 7B includes 24 pores 765, and since the 24 pores can be evenly divided into thirds, the three protrusions 757 of the stent engagement member 723 can be radially evenly spaced while each being aligned with one of the pores 765. Similarly, since the stent 805 of FIG. 8B includes 24 pores 865, and since the 24 pores can be evenly divided into sixths, the six protrusions 857 of the stent engagement member 823 can be radially evenly spaced while each being aligned with one of the pores 865. In other embodiments, the number of protrusions can be two, four, or eight, and the protrusions can be evenly spaced around the stent engagement member.

In other embodiments, the number of protrusions of the stent engagement member and the number and/or location of pores defined by the overlying stent can be such that even radial spacing of the protrusions would be disadvantageous. For example, a braided stent with 48 wires (and 24 pores) can be used with a stent engagement member that has 5 protrusions, in which case these protrusions cannot be evenly spaced around the engagement member and still each be aligned with pores of the stent. As another example, a braided stent with 54 wires will define 27 pores at a particular longitudinal position of the stent. Since the 27 pores cannot be evenly divided among four, five, or six protrusions, the protrusions may instead be unevenly radially spaced. In yet another example, a 64-wire stent will have 32 pores, which cannot be evenly divided among three, five, or six protrusions. In each of these cases, it can be advantageous to provide a stent engagement member with protrusions that are unevenly spaced apart from one another around a circumference of the engagement member. Similarly, in the case of a laser-cut stent, the pores may not be evenly radially spaced around the circumference of the device, and a stent engagement member with unevenly radially spaced can be useful with such a stent.

FIGS. 9A-10B illustrate two embodiments of such stent engagement members with unevenly spaced protrusions. Embodiments of the stent engagement members 923, 1023 described herein can be similar to the stent engagement members 123, 223, 723, and 823 described above, except that at least some embodiments can include unevenly spaced protrusions. FIGS. 9A and 9B illustrate side and bottom views, respectively, of the stent engagement member 923, which includes a six protrusions 957*a-f* separated by six recesses 959*a-f*. As shown in FIG. 9A, the recesses 959*a-f* can be shaped and sized differently from one another such that the protrusions 959*a-f* are not evenly spaced around the periphery of the engagement member 923. For example, the space or angular separation between the first protrusion 957*a* and second protrusion 957*b* is less than the space or angular separation between the second protrusion 957*b* and the third protrusion 957*c*. In one example, the angle between the first protrusion 957*a* and the second protrusion 957*b* can be 55.8 degrees, while the angle between the second protrusion 957*b* and the third protrusion 957*c* can be 68.5 degrees. This varied spacing can be achieved, e.g., by varying the structure of the individual recesses 959*a-f*. For example, each recess 959*a-f* can include a concave surface which curves inwardly between adjacent protrusions 959*a-f*. Certain recesses can have a larger surface area and/or a larger radius of curvature than other protrusions, thereby extending the radial spacing between adjacent protrusions. For example, the second recess 959*b* has both a greater surface area and a greater radius of curvature than the first recess 959*a*. This structure results in the spacing between the first and second protrusions 957*a* and 957*b* being smaller than the spacing between the second and third protrusions 957*b* and 957*c*. In the illustrated embodiment, the first recess 959*a*, third recess 959*c*, fourth recess 9859*d*, and sixth recess 959*d* are similarly configured to provide corresponding radial spacing between adjacent protrusions of approximately 55.8 degrees, while the second recess 959*b* and the fifth recess 959*e* are similarly configured to provide corresponding radial spacing between adjacent protrusions of approximately 68.5 degrees. This provides radial symmetry about certain axes, while also providing uneven spacing for improved engagement with an overlying stent. Other variations are possible, in which the particular angles between adjacent protrusions can be varied within ranges such that each protrusion 957*a-f* is configured to project into or mechanically interlock with a pore of an overlying stent.

As seen best in FIG. 9B, the engagement member 923 includes opposing first and second end faces 951, 953, with a side surface 955 extending between the two. The protrusions 957*a-f* and the recesses 959*a-f* can all be disposed along the side surface 955. In some embodiments, the edge formed at the intersection of the first end face 951 and the side surface 955 and the edge formed at the intersection of the second end face 953 and the side surface 955 can both be rounded. In particular, the edges at the projections 957*a-f* can be rounded, since in at least some embodiments only these outermost portions of the engagement member 923 contact (or otherwise engage with) an overlying stent or catheter. In contrast to embodiments in which there is a sharp edge between these surfaces (e.g., approximately a right-angle between two planar and orthogonal surfaces), the rounded edges can reduce scraping against a catheter inner wall, reducing damage and generation of particulate matter when an overlying catheter is moved with respect to the engagement member 923.

FIGS. 10A and 10B illustrate side and bottom views, respectively, of another embodiment of a stent engagement member 1023 with five protrusions 1057*a-e* that are unevenly spaced apart from one another by five recesses 1059*a-e*. The recesses 1059*a-e* can be shaped and sized differently from one another such that the protrusions 1059*a-e* are not evenly spaced around the periphery of the engagement member 1023. Rather, angle between the first protrusion 1057*a* and second protrusion 1057*b*, and the angle between the first protrusion and the fifth protrusion 1057*e*, can each be approximately 78.8 degrees. In contrast, the angle between the second protrusion 1057*b* and the fourth protrusion 1059*b*, and the angle between the fourth protrusion 1057*d* and the fifth protrusion 1057*e*, can each be approximately 67.7 degrees. Finally, the angle between the third protrusion 1057*c* and the fourth protrusion 1057*d* can be approximately 66.9 degrees. This varied spacing can be achieved by varying the structure of the individual recesses 1059*a-e*. For example, the first recess 1059*a* has both a greater surface area and a greater radius of curvature than the second recess 1059*b*, resulting in the spacing between the first and second protrusions 1057*a* and 1057*b* being greater than the spacing between the second and third protrusions 1057*b* and 1057*c*. Other variations are possible, in which the particular angles between adjacent protrusions can be varied within ranges such that each protrusion 1057*a-e* is configured to project into or mechanically interlock with a pore of an overlying stent.

As seen best in FIG. 10B, the engagement member 1023 includes opposing first and second end faces 1051, 1053, with a side surface 1055 extending between the two. The protrusions 1057*a-e* and the recesses 1059*a-e* can all be disposed along the side surface 1055. As discussed above with reference to FIG. 9B, in some embodiments, the edges formed at the intersection of the first end face 1051 and the side surface 1055 and formed at the intersection of the second end face 1053 and the side surface 1055 can be rounded to reduce friction and damage to an overlying catheter or the stent.

Figure 11C:
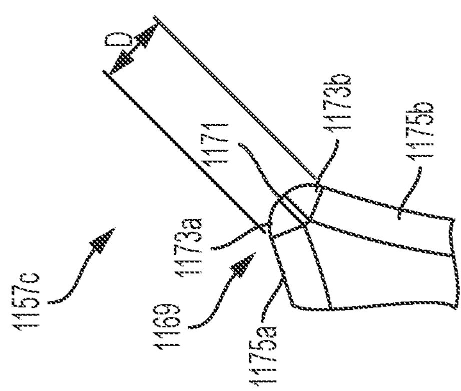
FIGS. 11A-11C illustrate enlarged detail views of portions of stent engagement members in accordance with different embodiments.
Figure 11B:
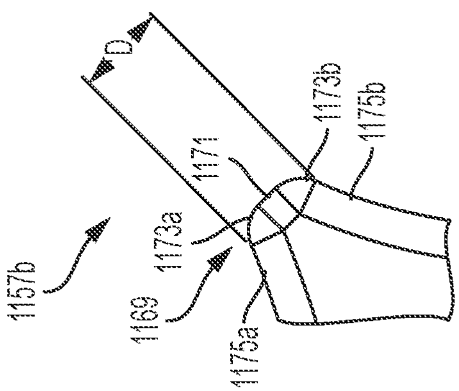
Figure 11A:
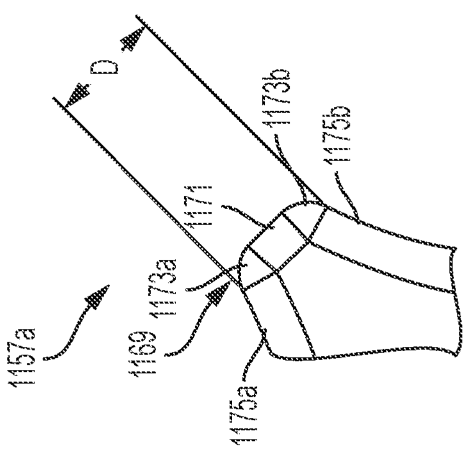

FIGS. 11A-11C illustrate enlarged detail views of projections 1157*a-c* of stent engagement members in accordance with different embodiments. As described above with respect to engagement members 123, 223, 723, 823, 923, and 1023, engagement members can include a plurality of projections separated by recesses. The projections can form the radially outer-most components of the stent engagement members, which in use can contact an overlying stent or otherwise interlock with it, in cooperation with an overlying catheter inner wall. The projections 1157*a-c* each include an outermost contact region 1169, characterized by a length D, which is configured to contact (or otherwise engage with) an overlying stent. The contact region 1169 can include a central portion 1171 flanked by opposing shoulder portions 1173*a* and 1173*b*. The shoulder portions 1173*a* and 1173*b* can extend between the central portion 1171 and opposing extensions 1175*a* and 1175*b*. The extensions 1175*a* and 1175*b* extend away from the contact region 1169 and towards corresponding recesses (not shown) of the stent engagement member. The central portion 1171 can have a substantially planar outermost surface, which can be coplanar with the adjacent shoulder portions 1173*a* and 1173*b*. However, the shoulder portions 1173*a* and 1173*b* can have curved outer surfaces which joint the central portion 1171 and the adjacent extensions 1175*a* and 1175*b*.

Together, the central portion 1171 and shoulder portions 1173*a*, 1173*b* define the length D of the contact region 1169. In certain embodiments, it can be advantageous to increase the overall surface area of the contact region 1169 by increasing the length D as compared to embodiments in which there is little or no central portion 1171. Among the embodiments shown in FIGS. 11A-C, the length D of the contact region 1169 is varied such that the length D is greatest in the protrusion 1157*a* of FIG. 11A, then smaller in the protrusion 1157*b* of FIG. 11B, and smallest in the protrusion 1157*c* of FIG. 11C. As a result, the protrusion 1157*a* has the greatest surface area configured to contact an overlying stent or catheter, followed by protrusion 1157*b* which has a smaller surface area configured to contact an overlying stent or catheter, and finally protrusion 1157*c* having a still smaller surface area configured to contact an overlying stent or catheter. In various embodiments, the length D of the contact region 1169 can be between about 0.001"-0.004", or between about 0.002"-0.003". For example, in some embodiments the contact region 1169 can have a length D of about 0.002", about 0.0025", or about 0.003". As will be appreciated, the various embodiments of the contact region 1169 can generally comprise a flat or planar central region, and first and second shoulders on either side of the central region. The shoulders can be rounded in up to two directions (radially as seen in FIGS. 11A-11C, and/or axially as seen in FIGS. 9B and 10B).

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A stent delivery system comprising:

a core member configured for advancement within a corporeal lumen;

a coupling assembly positioned about the core member, the coupling assembly comprising:

a distal restraint non-slidably coupled to the core member;

a first plate rotatably positioned about the core member proximal of the distal restraint, the first plate including an outer surface having three or more projections separated by recesses;

a coil spacer rotatably and non-slidably positioned about the core member proximal of and adjacent to the first plate; and a stent extending along the core member such that the stent is engaged by one or more projections of the first plate extending into a pore of the stent and is thereby distally advanceable via the core member, wherein the first plate is configured to longitudinally slide with respect to the core member over a limited range of motion between the coil spacer and the distal restraint, and wherein the first plate is configured to tilt with respect to a longitudinal axis of the core member.

2. The system of claim 1, wherein the coil spacer comprises a zero-pitch coil.

3. The system of claim 1, wherein the coil spacer is axially substantially incompressible.

4. The system of claim 1, further comprising a proximal restraint coupled to the core member, and wherein the coil spacer comprises a flattened proximal end face configured to abut against the proximal restraint.

5. The system of claim 1, wherein the coil spacer comprises a flattened distal end face configured to abut against the first plate.

6. The system of claim 1, wherein an outer diameter of the coil spacer is less than or equal to a recess diameter of the first plate.

7. The system of claim 1, wherein the coil spacer comprises a wire having a square or rectangular cross section that is wound into a coil configuration.

8. The system of claim 1, wherein the coil spacer comprises a wire that is wound into a coil configuration and the wound wire forms a number of winds, each with flat distal and proximal faces, wherein the faces of adjacent winds contact each other to enable the coil spacer to bear longitudinally compressive loads without shortening.

9. The system of claim 1, wherein the coupling assembly further comprises a second plate rotatably positioned about the core member, the second plate including an outer surface having three or more projections separated by recesses, and wherein one or more of the projections of the second plate engages the stent such that the stent is distally advanceable via the core member.

10. The system of claim 9, wherein the second plate is configured to longitudinally slide with respect to the core member over a limited range of motion and is configured to tilt with respect to the longitudinal axis of the core member.

11. The system of claim 9, wherein the coupling assembly further comprises a second spacer positioned about the core member and disposed between the first plate and the second plate.

12. The system of claim 11, wherein the second spacer comprises a second coil spacer.

13. The system of claim 11, wherein the second spacer comprises a solid tubular member.

14. A medical device delivery system, comprising:

a core member;

a coupling assembly carried by the core member, the coupling assembly comprising:

a distal restraint non-slidably coupled to the core member;

a first device engagement member rotatably coupled to the core member and disposed proximal to the distal restraint, the first device engagement member including an outer surface having projections separated by recesses; and a coil spacer rotatably coupled to the core member and disposed proximal of and adjacent to the first device engagement member, wherein the first device engagement member is configured to longitudinally slide with respect to the core member over a limited range of motion between the coil spacer and the distal restraint, and wherein the first device engagement member is configured to tilt with respect to a longitudinal axis of the core member; and an expandable medical device extending along the core member such that the medical device is engaged by one or more projections of the first device engagement member extending into a pore of the medical device and is thereby distally advanceable via the core member.

15. The system of claim 14, wherein the coil spacer comprises a zero-pitch coil.

16. The system of claim 14, wherein the coil spacer comprises a flattened proximal end face configured to abut against a proximal restraint coupled to the core member.

17. The system of claim 14, wherein the coil spacer comprises a flattened distal end face configured to abut against the first device engagement member.

18. The system of claim 14, wherein an outer diameter of the coil spacer is less than or equal to a recess diameter of the first device engagement member.

19. The system of claim 14, wherein the first device engagement member comprises a rigid plate or sprocket.

20. The system of claim 14, wherein the coil spacer comprises a wire having a square or rectangular cross section that is wound into a coil configuration.

21. The system of claim 14, wherein the coil spacer comprises a wire that is wound into a coil configuration and the wound wire forms a number of winds, each with flat distal and proximal faces, wherein the faces of adjacent winds contact each other to enable the coil spacer to bear longitudinally compressive loads without shortening.

22. The system of claim 14, wherein the coupling assembly further comprises a second device engagement member rotatably positioned about the core member, the second device engagement member including an outer surface having three or more projections separated by recesses.

23. The system of claim 22, wherein the medical device is engaged by one or more projections of the second device engagement member extending into a pore of the medical device, and is thereby distally advanceable via the core member.

24. The system of claim 22, wherein the coupling assembly further comprises a second spacer positioned about the core member and disposed between the first device engagement member and the second device engagement member.

* * * * *